US007868162B2

(12) United States Patent
Dale

(10) Patent No.: US 7,868,162 B2
(45) Date of Patent: Jan. 11, 2011

(54) ANTIMICROBIAL AND ANTIVIRAL COMPOUNDS AND METHODS FOR THEIR USE

(75) Inventor: Roderic M. K. Dale, Wilsonville, OR (US)

(73) Assignee: Lakewood-Amedex, Inc., Sarasota, FL (US)

( * ) Notice: Subject to any disclaimer, the term of this patent is extended or adjusted under 35 U.S.C. 154(b) by 775 days.

(21) Appl. No.: 11/552,951

(22) Filed: Oct. 25, 2006

(65) Prior Publication Data

US 2007/0053971 A1 Mar. 8, 2007

Related U.S. Application Data

(63) Continuation-in-part of application No. 10/937,094, filed on Sep. 8, 2004, now Pat. No. 7,176,191, which is a continuation of application No. 09/847,654, filed on May 3, 2001, now abandoned, which is a continuation-in-part of application No. 09/281,858, filed on Mar. 31, 1999, now Pat. No. 6,627,215, which is a continuation-in-part of application No. 09/222,009, filed on Dec. 30, 1998, now Pat. No. 6,211,349.

(51) Int. Cl.
*C07H 19/10* (2006.01)
*C07H 19/048* (2006.01)
*C07H 1/00* (2006.01)

(52) U.S. Cl. ................................. 536/26.8; 536/1.11
(58) Field of Classification Search .................. None
See application file for complete search history.

(56) References Cited

U.S. PATENT DOCUMENTS

| 4,105,782 | A | 8/1978 | Yu et al. |
|---|---|---|---|
| 4,421,769 | A | 12/1983 | Dixon et al. |
| 4,464,392 | A | 8/1984 | Bailey et al. |
| 4,897,355 | A | 1/1990 | Eppstein et al. |
| 4,908,209 | A | 3/1990 | McIntosh, Jr. et al. |
| 5,030,659 | A | 7/1991 | Bansemir et al. |
| 5,153,000 | A | 10/1992 | Chikawa et al. |
| 5,153,230 | A | 10/1992 | Jaffery |
| 5,294,533 | A | 3/1994 | Lupski et al. |
| 5,360,797 | A | 11/1994 | Johnson et al. |
| 5,420,330 | A | 5/1995 | Brush |
| 5,510,104 | A | 4/1996 | Allen |
| 5,603,915 | A | 2/1997 | Nelson et al. |
| 5,652,266 | A | 7/1997 | Bobier-Rival et al. |
| 5,739,309 | A | 4/1998 | Dattagupta et al. |
| 5,747,256 | A | 5/1998 | Yan et al. |
| 5,763,468 | A | 6/1998 | Barranx et al. |
| 5,767,054 | A | 6/1998 | Sprugel et al. |
| 5,830,140 | A | 11/1998 | Dillinger et al. |
| 5,843,998 | A | 12/1998 | Song et al. |
| 6,211,162 | B1 | 4/2001 | Dale et al. |
| 6,211,349 | B1 | 4/2001 | Dale et al. |
| 6,627,215 | B1 | 9/2003 | Dale et al. |
| 7,176,191 | B2 | 2/2007 | Dale et al. |
| 2002/0032164 | A1 | 3/2002 | Dale et al. |
| 2005/0025815 | A1 | 2/2005 | Dale et al. |
| 2009/0092659 | A1 | 4/2009 | Dale et al. |

FOREIGN PATENT DOCUMENTS

| EP | 0018492 A1 | 11/1980 |
|---|---|---|
| WO | WO-89/01023 A1 | 2/1989 |
| WO | WO-90/14074 A1 | 11/1990 |
| WO | WO-91/16024 A1 | 10/1991 |
| WO | WO-91/17424 A1 | 11/1991 |
| WO | WO-94/08563 A1 | 4/1994 |
| WO | WO-94/15619 A1 | 7/1994 |
| WO | WO-96/29399 A1 | 9/1996 |
| WO | WO-98/03533 A1 | 1/1998 |
| WO | WO-98/23294 A1 | 6/1998 |
| WO | WO-00/40591 A1 | 7/2000 |
| WO | WO-00/57890 A1 | 10/2000 |
| WO | WO-02/080668 A2 | 10/2002 |
| WO | WO-02/089581 A1 | 11/2002 |
| WO | WO-2008/133704 A2 | 11/2008 |

OTHER PUBLICATIONS

Dale et al., "Therapeutic Efficacy of Nubiotics against Burn Wound Infection by *Pseudomonas aeruginosa*", Antimicrobial agents and Chemotherapy, Aug. 2004, vol. 48, No. 8, pp. 2918-2923.*
McCutcheon's, vol. 2 Functional Materials, North American Edition, 137-168 (1992).
Wenninger, et al., CTFA Cosmetic Ingredient Handbook, Second Edition, The Cosmetic, Toiletry and Fragrance Association, Washington, D.C., 572-575 and 580 (1992).
Archer et al., *Antimicrob. Agents Chemother.* 38:2231-2237 (1994).
Bennett, *Antisense Res. Devel.* 3:235-241 (1993).
Burns et al., Advances in Pediatric Infectious Diseases 8:53-67 (1993).
Cameron, British Journal of Theatre Nursing 7(5):5-7 (Aug. 1997).
Cohen, Oligodeoxynucleotides; *Antisense Inhibitors of Gene Expression*, Boca Raton, FL, CRC Press. (1989).
Crooke, Antisense Nucleic Acid and Antisense RNA: Novel Pharmacological and Therapeutic Agents, B. Weiss ed., CRC Press Boca Raton, FL., p. 17 (1997).
Eck et al., Goodman & Gilman's The Pharmacological Basis of THerapeutics, Ninth Edition, McGraw-Hill, New York, p. 77-101 (1996).

(Continued)

*Primary Examiner*—Traviss C McIntosh, III
(74) *Attorney, Agent, or Firm*—Mintz Levin Cohn Ferris Glovsky and Popeo, P.C.; Ingrid A. Beattie, Esq.

(57) ABSTRACT

The present invention provides protonated compounds having antiviral and antimicrobial activity. The invention also provides antimicrobial compositions comprising protonated compounds of the invention. The protonated compounds of the invention provide efficacious antimicrobial activity against resistant strains of bacteria and opportunistic fungi. The invention also provides antiviral compositions comprising compounds of the invention. Viruses that may be treated by compositions of the invention include, but are not limited to, HIV, HSV, CMV, HBV, HCV and influenza virus.

3 Claims, 8 Drawing Sheets

OTHER PUBLICATIONS

Freelander, *Hosp Med* 59(6):484-487 (Jun. 1998).
Goth, Medical Pharmacology: Principles and Concepts, The C.V. Mosby Company, Saint Louis, MO..(1974).
Gould, et al., *Lancet*, 22:1377-79 (1981).
Heidenreich et al., *Molecular Medicine Today*, vol. 1(3):128-133 (1995).
Hoke et al., *Nucl. Acids Res.* 19:5743 (1991).
Hughes et al., *Pharmaceutical Research* 12:817 (1995).
Jones et al., *Nurs Stand* 12(39):47-52 (Jun. 17-23, 1998).
Krieg et al., *Nature* 374:546-549 (1995).
Kristinsson, *Microb. Drug Resistance* 1(2):121 (1995).
Levy et al., *J. Infect. Dis.*, 148:1069-1076 (1983).
Mastrangelo et al., *Seminars in Oncology*, 23 (1):4-21 (Feb. 1996).
Pennington, *Rev. Infect. Dis.*, 3:67-73 (1981).
Spotnitz et al., *Surg Clin North Am* 77(3):651-69 (Jun. 1997).
Staley et al., *Adv Wound Care* 10(2):39-44 (Mar.-Apr. 1997).
Ther Merck Index, 12th edition, pp. 1490-1491; 763-764 (1996).
Verma et al., *Nature*, 389:239-242 (Sep. 1997).
Woodford et al., *J. Antimicrob. Chemother.* 35:179-184 (1995).
Wu-Pong, S., *Pharmaceutical Technology*, Oct., p. 102, 104, 106, 108, 110-112, 114 (1994).
Yamamoto et al., *Antisense Res. Devel.* 4:119-122 (1994).
Zabransky et al., *J. Clin. Microbiol.* 33(4):791-793 (1995).
Zimmer et al., *Biopolymers*, 6(4):563-574 (1968).
Morbidity and Mortality Weekly Report, 45(6):121-144 (1996).
Reed et al., "A Simple Method of Estimating Fifty Percent Endpoints" *Amer. J. Hyg.*, 27(3):493-497 (1938).
Snoeck, et al., "(S)-1-(3-Hydroxy-2-Phosphonylmethoxypropyl) Cytosine, a Potent and Selective Inhibitor of Human Cytomegalovirus Replication", *Antimicrobial Agents and Chemotherapy*, 32(12):1839-1844 (1988).
T.W. Graham Solomans, Organic Chemistry, John Wiley and Sons, Inc., New York 6th ed. pp. 937-971 (Jul. 1998).

* cited by examiner pyridine        pyrazine        triazine quinoline isoquinoline quinazoline pteridine indole indazole acridine phenothiazine phenoxazine phenazine piperazine
hydrogenated pyrazine piperidine
(hydrogenated pyridine)

caprolactam leucomethylene blue

ANTIMICROBIAL AND ANTIVIRAL COMPOUNDS AND METHODS FOR THEIR USE

CROSS-REFERENCE TO RELATED APPLICATIONS

This application is a continuation-in-part of U.S. patent application Ser. No. 10/937,094, filed Sep. 8, 2004, now U.S. Pat. No. 7,176,191, which is a continuation of U.S. application Ser. No. 09/847,654, flied on May 3, 2001, now abandoned, which is in turn a continuation-in-part of U.S. patent application Ser. No. 09/281,858 filed Mar. 31, 1999, now U.S. Pat. No. 6,627,215, which application is a continuation-in-part of U.S. patent application Ser. No. 09/222,009 filed Dec. 30, 1998, now U.S. Pat. No. 6,211,349, all of which are herein incorporated by reference in their entirety.

FIELD OF THE INVENTION

The invention relates generally to the field of therapeutics used to treat bacterial, fungal and viral infections. The invention relates generally to the field of protonated chemicals and specifically to protonated compounds used as pH stabilizers and therapeutics containing such molecules.

BACKGROUND OF THE INVENTION

Pathogenic bacteria responsible for infectious diseases were once thought to be controllable through the use of a battery of antibiotics such as penicillin, streptomycin, tetracycline, and others. However, since the widespread use of antibiotics began in the 1950s, more and more bacteria have evolved to become resistant to one or more antibiotics. Multiple drug-resistant strains are increasingly common, particularly in hospitals.

Currently, nosocomial Staphylococcal infections exhibit multiple drug resistance. See, for example, Archer et al., 1994, *Antimicrob. Agents Chemother.* 38:2231-2237. At this time, the remaining antibiotic that demonstrates the ability to kill most strains of Staphylococci is vancomycin. However, vancomycin resistant strains of both *Staphylococcus* and *Enterococcus* have already been isolated and reported by Zabransky et al., 1995, *J. Clin. Microbiol* 33(4):791-793. Furthermore, transfer of resistance from Enterococci to Staphylococci has been previously documented by Woodford et al., 1995, *J Antimicrob. Chemother.* 35:179-184. *Streptococcus pneumoniae* is a leading cause of morbidity and mortality in the United States (M. M. W. R., Feb. 16, 1996, Vol. 45, No. RR-1). Each year these bacteria cause 3,000 cases of meningitis, 50,000 cases of bacteremia, 500,000 cases of pneumonia, and 7,000,000 cases of otitis media. Case fatality rates are greater than 40% for bacteremia and greater than 55% for meningitis, despite antibiotic therapy. In the past, *Streptococcus pneumoniae* were uniformly susceptible to antibiotics; however, antibiotic resistant strains have emerged and are becoming widespread in some communities.

In addition, there are instances where antibiotic resistance is not an issue, yet a particular bacterium remains refractory to treatment using conventional antibiotics. Such is the case with *Escherichia coli* O157:H7, a causative agent for food poisoning and death from undercooked meat. The Department of Agriculture estimates that 10 people die each day and another 14,000 become ill due to this bacterium. Unfortunately, conventional antibiotics are completely ineffective against this organism.

The history of antibiotic treatment of pathogenic bacteria is cyclical. Bacteria are remarkably adaptive organisms, and, for each new antibiotic that has been developed, resistant bacterial strains arise through the widespread use of the antibiotic. Thus, there is a constant need to produce new antibiotics to combat the next generation of antibiotic-resistant bacteria. Traditional methods of developing new antibiotics have slowed, and in the past two years, only one new antibiotic has been approved by the FDA. Furthermore, according to Kristinsson (*Microb. Drug Resistance* 1(2):121 (1995)), "there are no new antimicrobial classes with activity against resistant Gram positives on the horizon."

There is a need for a compound that provides a compositional environment that will allow an increase in the efficacy of known antibacterial agents. There is also a need in the art for a compound that facilitates the activity of an active antibacterial agent, thus allowing the use of a lower amount or dose of antibiotic while reducing the development of resistant bacterial strains.

Viral disease is another health related disease state which threatens large segments of human populations. Some of the features related to viral infection which are of concern to health care professionals include its highly contagious nature (i.e., HIV, SARS etc) and high mutability. Some viruses are also oncogenic (such as HPV, EBV and HBV). While viruses are structurally amongst the simplest of organisms, they are regarded to be among the most difficult to control and present a formidable challenge for antiviral drug R&D.

Thus far, there have been a few antiviral drugs widely used in patients, such as Amantadine for flu, Acyclovir for HSV-related infections, Ganciclovir for CMV infection, and AZT, DDI and d4T for AIDS treatments. These drugs possess a variety of undesirable neurological, metabolic and immunological side-effects. Therefore, development of new antiviral therapy has become a major focus of medical and pharmaceutical research and development.

Nucleosides are natural metabolic products and precursors in human and animals. Modified nucleosides may have much lower toxicity to humans and thus have potential for use as safer antiviral drugs.

SUMMARY OF THE INVENTION

The present invention provides molecules having antimicrobial activity, which molecules have two end blocks and at least one proton acceptor site. The invention also provides for compositions of the invention comprising a protonated antimicrobial compound and an excipient. The protonated compounds of the invention can be used as the sole active agent in the composition, or may be used in conjunction with another active agent to enhance the efficacy of compositions against resistant strains of bacteria and opportunistic fungi.

The structure of the compounds of the invention is X—Y—Z, where X and Z are end blocking groups, preferably alkyls or O-alkyls, which may be the same or different, and Y is a phosphorous containing molecule with protonation sites.

In a preferred embodiment, Y is one or more substituted or unsubstituted phosphate groups. Exemplary structures of this embodiment have a Y structure as follows (Structures 1 and 2):

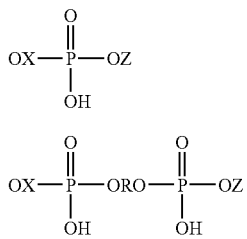

Structure 1

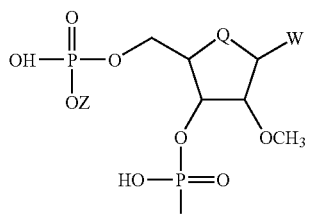

Structure 2 where X and Z are end blocking groups, which may be the same or different, and R is a dysfunctional alkyl, aryl, alkenyl (preferably containing 1-20 carbons, more preferably 1-6 carbons), or some combination of the three (e.g., a difunctional alkyl, aryl, alkenyl, alkylaryl, alkylalkenyl, arylalkenyl or alkylarylalkenyl group), as a derivative of primary, secondary or tertiary alcohols; phenols; or enols either separately or in any combination. It may be monocyclic, polycyclic, heterocyclic or linear in form, either separately or in any combination of forms. It may have free alcoholic or phenolic hydroxyls in addition to the two converted into phosphodiesters. There may be other functional groups such as but not limited to amines, carboxylates, carboxyaldehydes, ketones, and the structure may be modified by the addition of halogens or other groups intended to modify the electronegativity of the structure of the molecule.

In another embodiment, Y is a sugar structure, preferably pentose or hexose, flanked by substituted or unsubstituted phosphate groups. Examples of such sugar groups can be seen in Structures 3A, 3B below:

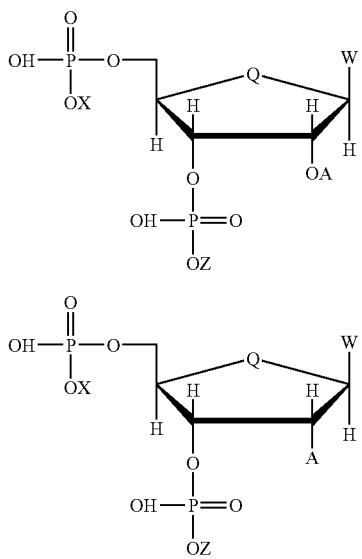

Structure 3A

Structure 3B wherein:

Q is O, S, P—H, P—OH, P-alkyl, P-aryl, P-acyl, N—H, N—OH, N-alkyl, N-aryl, or N-acyl;

A is H, alkyl, or alkyl-(O-alkyl), aryl, alkenyl, alkanol, phenol, or enol;

X and Z are end blocking groups that may be the same or different; and

W is H, or a purine or pyrimidine, or a modified analogue of a purine or pyrimidine.

Further examples of such sugar groups can be seen in Structures 4A and 4B below:

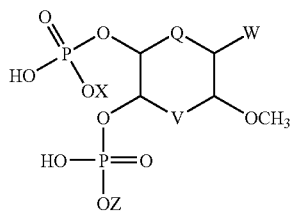

Structure 4A

Structure 4B wherein:

V or Q is independently O, S, P—H, P—OH, P-alkyl, P-aryl, P-acyl, N—H, N—OH, N-alkyl, N-aryl, or N-acyl, —CH2, —CH(OH)—, —CH2(O-alkyl)-;

X and Z are end blocking groups that may be the same or different; and

W is H, or a purine or pyrimidine, or a modified analogue of a purine or pyrimidine.

In a preferred embodiment, Q and/or V independently may be —CH$_2$—, —CH(OH)—, or —CH(O-alkyl)-.

In a preferred embodiment, the sugar is a pentose molecule with a substitution at the 2 carbon site (hereafter "2-R substituted" and the like), as illustrated as Structure 5:

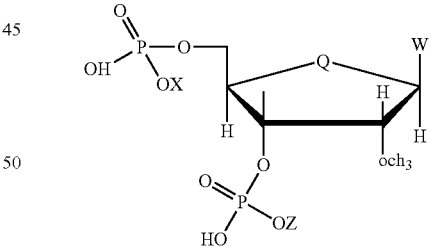

Structure 5

Wherein

Q is O, S, P—H, P—OH, P-alkyl, P-aryl, P-acyl, or N—H; and

W, X and Z are as stated above.

The X and Z groups are chemical moieties that provide stability. The end blocking groups may be any number of chemical entities, provided the end block prevents degradation of the molecule. In one embodiment, the end blocks are alkyl or O-alkyl, where the alkyl moiety can be straight chained, branched or cyclic but is preferably a straight chain containing 1-4 carbons. X and Z may be the same chemical moiety (e.g., butyl groups) or two different chemical moieties (e.g., X is a butyl group and Z is a butanol). In some embodiments, X and Y are independently $CH_3CH_2CH_2CH_2—$, $CH_3CH_2CH_2—$, $CH_3CH_2—$, $HO—CH_2CH_2CH_2CH_2—$, $XO—CH_2CH_2CH_2CH_2—$, or $YO—CH_2CH_2CH_2CH_2—$.

In a specific embodiment, the compound is a protonated molecule having end blocking groups to prevent degradation, and a sugar group with a 2-R or 2-OR modification. One example of such a molecule is shown as Structure 5. The protonated compounds of the invention are acidified to give a pH when dissolved in water of less than pH 6 to about 1, more preferably less than pH 4.5 to about 1, and even more preferably less than pH 3 to about 2. By introducing the modifications such as these to the compounds of the invention, the compounds are rendered more acid and nuclease resistant. Percent acid degradation may be determined using analytical HPLC to assess the loss of functional molecules, or by other suitable methods. The compounds of the invention are 10%, 20%, 30%, 40%, 50%, 70%, 90%, 100%, 150%, 200%, 300%, 500%, 750%, or 100% more stable than a reference compound.

In one aspect of the invention, the compounds of the invention are incorporated into liposomes. In some embodiments of the invention, neutral lipids, cholesterol, and/or polyethylene glycol (PEG) are utilized in the liposomes. In some embodiments the liposomal composition is composed of partially hydrogenated soy phosphatidylcholine (PHSC), cholesterol, methoxy-terminated PEG (mnPEG), and/or distearoyl phosphatidyl ethanolamine (DSPE). In some embodiments the ratio of PHSC:mnPEG:DSPE may be in the range of about 40:50:10 w/w % to about 60:30:10 w/w % or to about 60:35:5 w/w %. In some embodiments the percentage of PHSC is in the range of about 40% to about 60 w/w % of the total lipid content. In some embodiments the percentage of mPEG is in the range of about 25% to about 45 w/w % of the total lipid content. In some embodiments the percentage of DSPE is in the range of about 3% to about 15 w/w % of the total lipid content. In other embodiments, the liposome formulation comprises of partially hydrogenated soy phosphatidylcholine (PHSC), cholesterol, and methoxy-terminated PEG (mPEG). In some embodiments the ratio of PHSC:cholesterol:mnpEG may be in the range of about 40% to about 60 w/w % PHSC, about 30% to about 40 w/w % cholesterol, and about 5% to about 10 w/w % mPEG. In some other embodiments, the liposome formulation comprises about 56% PHSC, about 38% cholesterol and about 6% MPEG. In some embodiments of the invention, the liposomes have a particle size of about 60 nm to about 120 nm diameter. In other embodiments of the invention, the liposomes have a particle size of about 75 nm to 110 nm, or about 80 nm to about 100 nm. The ratio of a compound of the invention to lipids in the liposomal composition may be about 1:9 w/w to about 1:3 w/w. In some embodiments the ratio of a compound of the invention to lipids in the liposomal composition may be about 1:5 w/w to about 1:3 w/w. The liposomal compositions of the invention may further contain one or more excipients.

The invention also provides methods for inhibiting or preventing the growth of bacteria, fungus, or virus, by contacting the infectious organism with a composition comprising a protonated compound of the present invention. In some embodiments the methods are used to treat a mammal. In some embodiments, the methods are used to treat a human.

The invention provides methods using compounds of the invention to treat a mammal suffering from a bacterial infection caused by *Staphylococcus aureus, Streptococcus pyogenes, Streptococcus pneumoniae, Mycobacterium* and *Escherichia coli, Aerococcus, Listeria, Streptomyces, Chlamydia, Lactobacillus, Eubacteriur, Arachnid, Mycobacterium, Peptostreptococcus, Corynebacterium, Erysipelothrix, Dermatophilus, Rhodococcus, Pseudomonas, Streptococcus, Bacillus, Peptococcus, Pneumococcus, Micrococcus, Neisseria, Klebsiella, Kurthia, Nocardia, Serratia, Rothia, Escherichia, Propionibacterium, Actinomyces, Helicobacter, Enterococcus, Shigella, Vibrio, Clostridium, Salmonella, Yersinia*, or *Haemophilus*. An embodiment of the invention provides a method of treating a mammal suffering from a bacterial infection by administering a liposomal composition comprising the compound of Formula 1 and a lipid.

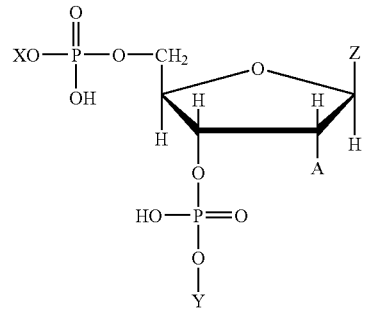

Formula I

The invention provides methods using compounds of the invention to treat a mammal suffering from a fungal infection caused by *Trichophyton, Epidermophyton, Microsporum, Candida, Pityrosporum, Trichophyton*, or *Epidermophyton*. An embodiment of the invention provides a method of treating a mammal suffering from a fungal infection by administering a liposomal composition comprising the compound of Formula 1 and a lipid.

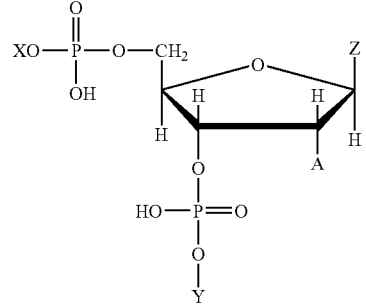

Formula I

The invention provides methods using compounds of the invention to treat a mammal suffering from a viral infection caused by HIV, HSV, CMV, HBV, HCV or influenza virus. An embodiment of the invention provides a method of treating a mammal suffering from a viral infection by administering a liposomal composition comprising the compound of Formula 1 and a lipid.

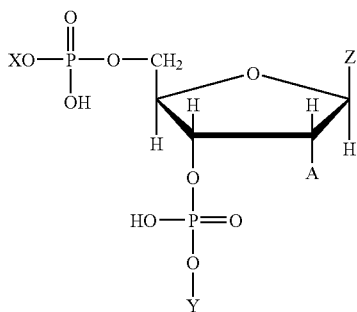

Formula I

In some embodiments of the invention the liposomal compositions are administered to a mammal orally. In some embodiments of the invention the liposomal compositions are administered to a mammal topically. In some embodiments of the invention, the liposomal compositions of the invention are administered to a mammal via aerosol. In some embodiments of the invention the liposomal compositions of the invention are administered via injection.

Administration of the composition will introduce the compounds of the invention to the mammal in a diluted amount. Exemplary unit dosages for oral, injectable, aerosol, or topical administration may be more than about 0.01, 0.05, 0.1, 0.5, 1, or 5 mg/kg, and/or less than about 10, 5, 1, 0.5, 0.1, or 0.05 mg/kg. Exemplary unit dosage ranges may be between about 0.01 mg/kg and 10 mg/kg, or between about 0.010 mg/kg and 1.0 mg/kg, or between about 0.10 mg/kg and 1.0 mg/kg. In some embodiments, the compositions of the invention are administered at unit dosages of about 0.01 to about 100 ug per kg of body weight, or about 0.1 to about 100 ug per kg of body weight, or about 0.1 to about 10 ug per kg of body weight, or about 1 to about 10 ug per kg of body weight, or about 1 to about 5 ug per kg of body weight. In some embodiments, unit dosages of the composition of the invention are at or below 100 ug per kg of body weight, or at or below 10 ug per kg of body weight, or at or below 1 ug per kg of body weight, or at or below 0.1 ug per kg of body weight, or at or below 0.01 ug per kg of body weight.

In some embodiments of the invention, one dosage unit may be administered once every 10, 9, 8, 7, 6, 5, 4, 3, 2, or one day, or 1, 2, 3, 4, 5, 6, 7, 8, 9, 10, or more than 10 times per day until relief is achieved or until the symptoms disappear or are satisfactorily attenuated. In some embodiments, one dosage unit is administered about once to about four times per day. In some embodiments, a patient is instructed to take two to three dosage units per day.

In some embodiments, the invention provides homeopathic compositions. Homeopathic compositions may be made by methods known in the art. One exemplary method of making a homeopathic composition comprises (i) triturating solid compound of the invention in a 1/9 ratio with lactose to produce a 1× solid and (ii) repeating the process until the desired attenuation is achieved. In a related vein, a method of making a homeopathic composition comprising (i) dissolving 1 part compound of the invention by weight in liquid to produce ten volumes of liquid attenuation labeled 1× and optionally (ii) mixing 1 ml of the 1× attenuation with 9 ml of diluent to produce a lower concentration, is also addressed.

The invention specifically provides therapeutic methods of using protonated compounds as inactive ingredients in topical compositions containing an active ingredient, e.g., an antibiotic, antifungal, or antiviral. The preferred method of treatment comprises the administration of the protonated compounds with an appropriate excipient to an animal. For example, the protonated compounds are administered to alleviate the symptom of the bacterial growth, or in an amount effective for treatment of a bacterial infection.

The invention further provides the use of the protonated compounds as an inactive biostatic or biocidal preservative in compositions, in conjunction with an acceptable pharmaceutical carrier, to prepare medicinal compositions for the treatment of bacterial infections in animals, and more preferably mammals, including humans.

The invention further provides the use of the protonated compounds as an active ingredient having antifungal properties against infectious agents such as *Candida albicans* and *Trichophyton*.

The invention further provides the use of the protonated compounds as an active ingredient having antiviral properties against infectious agents such as herpes simplex found in cold sores.

The invention further provides the use of the described protonated compounds as active ingredients in a topical skin cream with an acceptable cosmetic carrier. Such topical skin creams may contain additives such as emollients, moisturizers, fragrance, and the like.

The invention further provides disinfectant solutions comprised of the described protonated compounds. The disinfectant may be suitable for use on skin, due to the non-toxicity of the protonated compounds, or may be used for disinfection of a surface such as medical devices, e.g. a surgical instrument.

It is an object of the invention to use protonated compounds in conjunction with one or more antibacterial agents to inhibit the growth of any bacteria, including clinically relevant pathogenic bacteria.

It is an advantage of the invention that the mechanism of action of the activity of the protonated compounds is effective against any bacterium including clinically relevant pathogenic bacteria, both gram positive and gram negative.

It is another advantage of the invention that the protonated compounds are non-toxic to a subject treated with the a composition containing the protonated compounds These and other objects, advantages, and features of the invention will become apparent to those skilled in the art upon reading the details of the protonated compounds and uses thereof as more fully described below.

DESCRIPTION OF THE PREFERRED EMBODIMENTS

Figure 1:
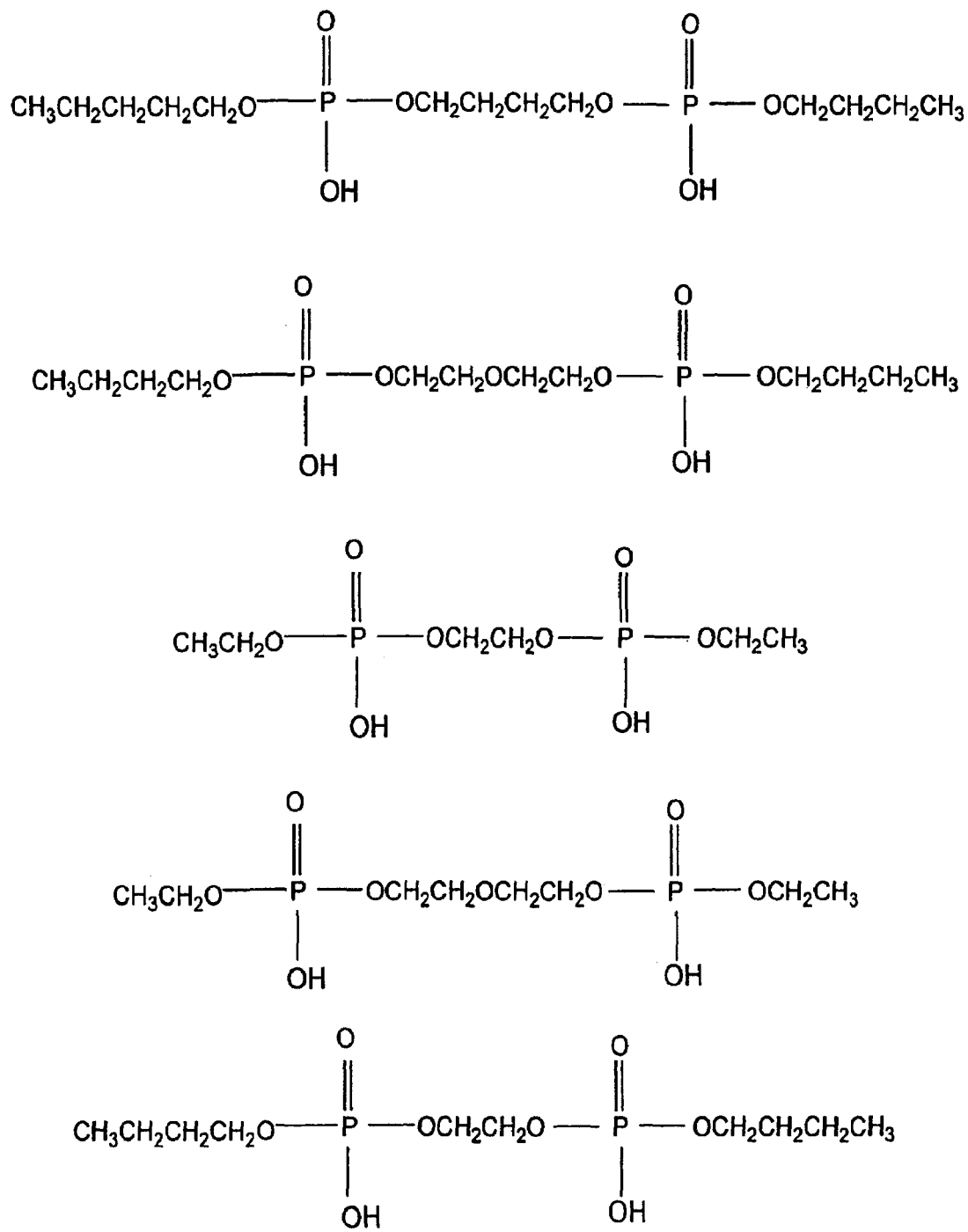
FIG. 1 illustrates the chemical structure of exemplary molecules of a preferred embodiment of the invention.
Figure 2:
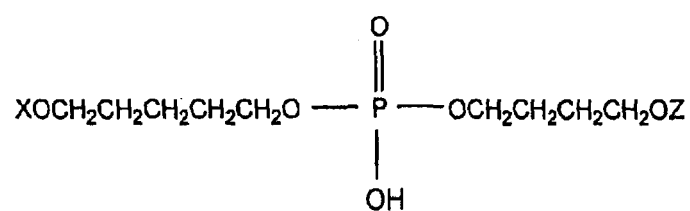
FIG. 2 illustrates alkyl phosphate structures that may be used as the central group (Y) in the compounds of the invention; X and Z are end blocking groups that may be the same or different.
Figure 2:
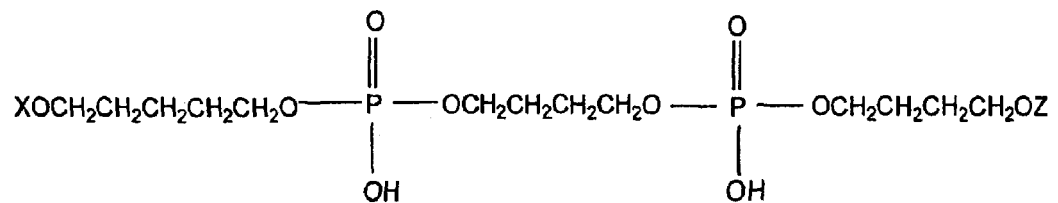
Figure 3:
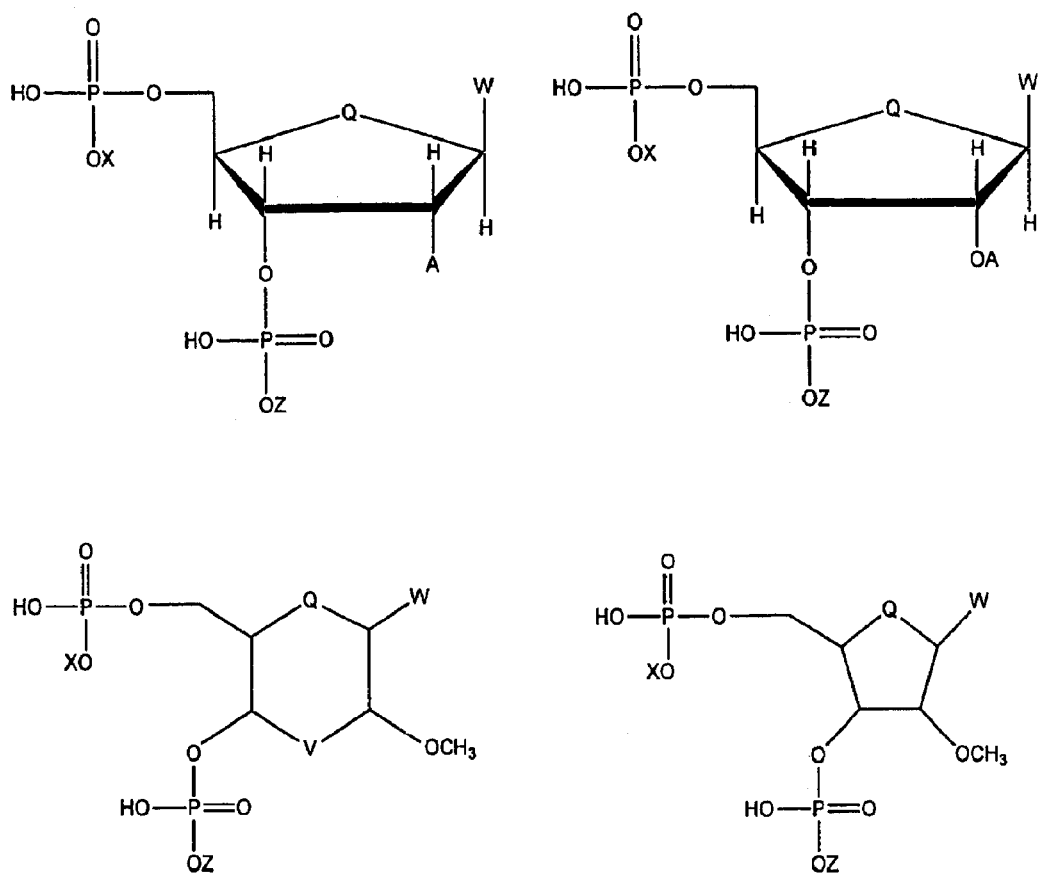
FIG. 3 illustrates exemplary sugar structures of the central group (Y) of molecules of the invention.

It is to be understood that this invention is not limited to the particular methodology, protocols, and reagents described, as such may, of course, vary. It is also to be understood that the terminology used herein is for the purpose of describing particular embodiments only, and is not intended to limit the scope of the present invention, which will be limited only by the appended claims.

It must be noted that as used herein and in the appended claims, the singular forms a, and, and the include plural referents unless the context clearly dictates otherwise. Thus, for example, reference to bacteria includes a plurality of bacteria species and a protonated compound may encompass a plurality of such compounds and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the active antibiotic agents, composition carriers, and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

DEFINITIONS

The term "antimicrobial" refers to an ability to kill or inhibit the growth of microorganisms (including, without limitation, viruses, bacteria, yeast, fungi, protozoa, etc.), or to attenuate the severity of a microbial infection. The antimicrobial compounds of the present invention are compounds that may be used in the treatment of disease and infection.

The term "protonation" and "acidification" as used interchangeably herein refers to the process by which protons (or positively charged hydrogen ions) are added to proton acceptor sites on a compound of the invention. The proton acceptor sites include the substituted or unsubstituted phosphates of the central group, as well as any additional proton acceptor sites on either the central group or the end blocking groups. As the pH of the solution is decreased, the number of these acceptor sites which are protonated increases, resulting in a more highly protonated compound.

The term "protonated compound" refers to a molecule of the invention that, when dissolved in water having a pH of 7 causes the pH of the solution to fall. Generally, compounds are protonated by adding protons to the reactive sites on the molecule, although other modifications of the molecule are possible, and are intended to be encompassed by this term. Such protonization can be accomplished, for example by incubating the compound in the presence of a strong acid, most preferably one with a volatile conjugate base.

The term "end group" and "end blocking group," as used herein refers to any chemical moiety that prevents substantial nuclease degradation, and in particular exonuclease degradation, of a protonated compound. The end group may be any chemical moiety that allows for proper protonation of the compound, including H, OH, SH, NH2, an alkyl group, an alkanol group, and the like. In a specific embodiment, the chemical modification is positioned such that it protects the central group of the molecule, i.e. the blocking group is the X or Z that protects the central group Y of the X—Y—Z structure. The end group(s) and/or end-blocking group(s) of an X—Y—Z molecule may be the same or different.

The term "active agent" as used herein, refers to compounds with known activity for the treatment of disease caused by microbes, and in particular agents that are effective in sublingual, intraocular, intraaural, and particularly topical, application.

Central or end groups may contain chemical moieties such as phosphodiesters, methylphosphonates, ethylphosphotriesters, methylphosphorothioates, methyl-p-ethoxy groups, methyls, alkyls, O-alkyls, O-alkyl-n(O-alkyl), fluorines, deoxy-erythropentofuranosyls, methyl ribonucleosides, methyl carbamates, methyl carbonates, inverted bases (e.g., inverted T's), etc. In one preferred embodiment, these chemical moieties contain oxygen linkages groups, e.g. O-methyl or O-alkyl-n(O-alkyl).

The term "alky!" as used herein refers to a straight chain, cyclic, branched or unbranched saturated or unsaturated hydrocarbon chain containing 1-20 carbon atoms (preferably 1-6), such as methyl, ethyl, propyl, tert-butyl, n-hexyl and the like.

The term "alkanol" as used herein refers to a branched or unbranched hydrocarbon chain containing 1-6 carbon atoms and at least one —OH group, such as methanol, ethanol, propanol, isopropanol, butanol, and the like.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease (or infection) and/or adverse effect attributable to the disease (or infection). "The terms "treatment", "treating" and the like as used herein includes:

(a) preventing a microbial disease and/or infection from occurring in a subject who may be predisposed to but has not yet been diagnosed as having it;

(b) inhibiting the progress or transmission of a microbial disease and/or infection, i.e., arresting its development or maintenance; or (c) relieving a bacterial disease (i.e., causing regression and/or amelioration of the disease) and/or infection.

The term "treatment" further comprises preventing inhibiting or relieving the symptoms of a disease resulting from infection by a microbe. The invention is particularly directed toward treating patients with any infectious bacteria or fungi; in a mammal, and particularly in a human mammal.

The present invention employs protonated compounds as antimicrobial agents, and in particular as antimicrobial agents having activity against bacteria, fungi, protozoa and viruses. These compounds are particular useful in medical applications, both allopathic and homeopathic. The bacteriocidal/bacteriostatic effect also allows use of these compositions in compositions for sterilization (e.g., sterilization of skin or of a surface or an object such as a surgical instrument, etc.), or sanitization (e.g., the cleansing of a surface, instrument, etc. so as to render it free of undesirable concentrations of disease causing microorganisms (including viruses). In addition, the protonated compounds themselves in specific concentrations have an antimicrobial preservative effect, and thus are also useful in preventing unwanted microbial growth in compositions.

I. DETAILED DESCRIPTION OF THE COMPOUNDS OF THE INVENTION

A. The Structures of the Compounds of the Invention

The protonated compounds of the invention have a structure as follows:

X—Y—Z primary, secondary or tertiary alcohols; phenols; or enols either separately or in any combination. It may be monocyclic, polycyclic, heterocyclic or linear in form, either separately or in any combination of forms. It may have free alcoholic or phenolic hydroxyls in addition to the two converted into phosphodiesters. There may be other functional groups such as but not limited to amines, carboxylates, carboxyaldehydes, ketones, and the structure may be modified by the addition of halogens or other groups intended to modify the electronegativity of the structure of the molecule.

Examples of molecules that are intended to be encompassed by the above-described structures include:

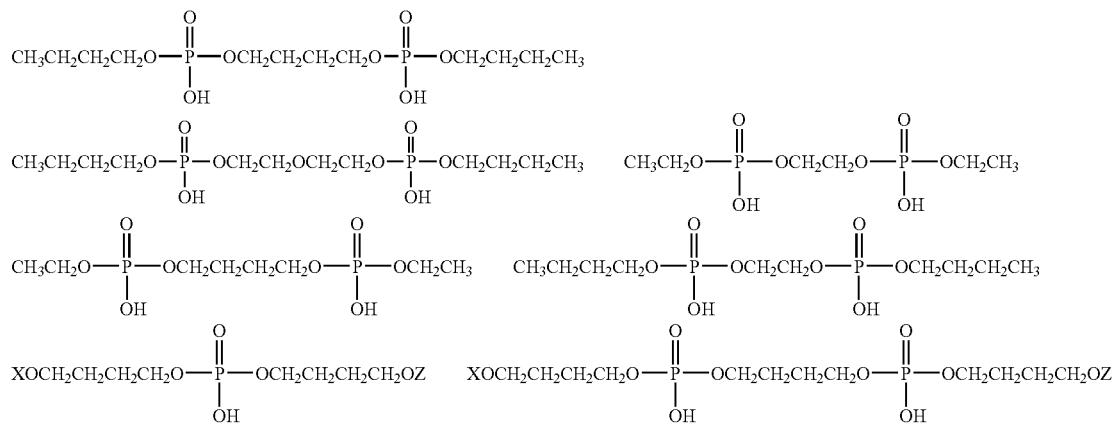

where Y is a structure comprising oxygen, phosphorous, and optionally carbon and X and Z are end groups comprising a blocking agent. The end groups X and Z may be the same chemical moiety, or they may be different.

In a preferred embodiment, Y is one or more substituted or unsubstituted phosphate groups. Exemplary structures of this embodiment have a Y structure as follows (Structures 1 and 2):

Structure 1

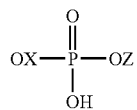

Structure 2

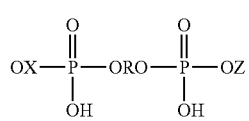

where X and Z are end blocking groups, which may be the same or different, and R is a difunctional alkyl, aryl, alkenyl (preferably containing 1-20 carbons, more preferably 1-6 carbons), or some combination of the three, as a derivative of A particularly preferred example of such compounds is Nu-5:

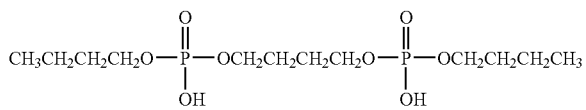

In another embodiment, Y is a sugar structure, preferably pentose or hexose, flanked by substituted or unsubstituted phosphate groups. Examples of X—Y—Z compounds containing such Y sugar groups are illustrated below:

and

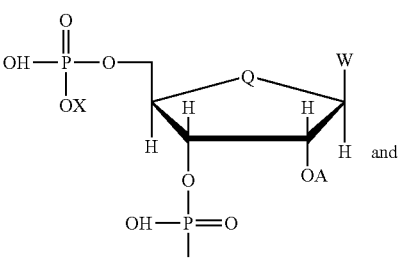

-continued

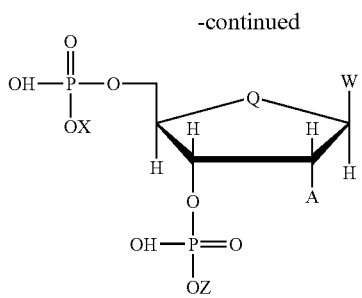

Wherein:

Q is O, S, P—H, P—OH, P-alkyl, P-aryl, P-acyl, N—H, N—OH, N-alkyl, N-aryl, or N-acyl;

A is H, alkyl, alkoxy, or alkyl-(O-alkyl), aryl, alkenyl, alkanol, phenol, or enol;

X and Z are end blocking groups that may be the same or different; and

W is H, or a purine or pyrimidine, or a modified analogue of a purine or pyrimidine.

Preferred examples of such compounds have X or Z blocking groups, which independently comprise a structure selected from the group consisting:
CH₃CH₂CH₂CH₂—; CH₃CH₂CH₂—; CH₃CH₂—; HO—CH₂CH₂CH₂CH₂—; XO—CH₂CH₂CH₂CH₂—; and ZO—CH₂CH₂CH₂CH₂—.

Preferred examples of such compounds have an A group, which comprises a structure selected from the group consisting: —H; —CH₃; —OCH₂CH₂OCH₂CH₃; and —OCH₂CH₃.

Further examples of X—Y—Z compounds containing such Y sugar groups are illustrated below.
and

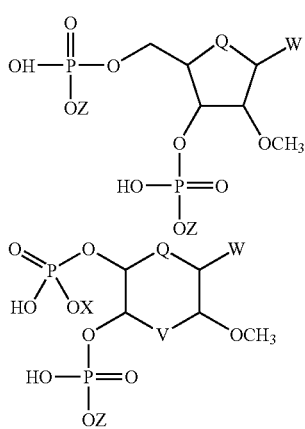

Wherein:

V or Q is independently O, S, P—H, P—OH, P-alkyl, P-aryl, P-acyl, N—H, N—OH, N-alkyl, N-aryl, N-acyl, —CH2-, —CH(OH)—, —CH(O-alkyl)-;

X and Z are end blocking groups that may be the same or different; and

W is H, or a purine or pyrimidine, or a modified analogue of a purine or pyrimidine.

Preferred examples of such compounds have X or Z blocking groups, which independently comprise
CH₃CH₂CH₂CH₂—; CH₃CH₂CH₂—; CH₃CH₂—; HO—CH₂CH₂CH₂CH₂—; XO—CH₂CH₂CH₂CH₂—; or ZO—CH₂CH₂CH₂CH₂—.

In a preferred embodiment, the sugar is a pentose molecule with a substitution at the 2 carbon site (hereafter "2-R substituted" and the like), as illustrated as Structure 5:

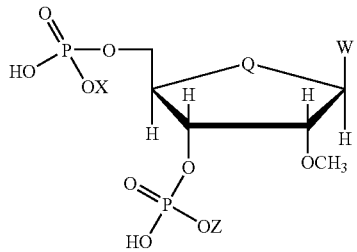

Structure 5

Q is O, S, P—H, P—OH, P-alkyl, P-aryl, P-acyl, or N—H;
W, X and Z are as stated above.

The X and Z groups are chemical moieties that provide stability. The end blocking groups may be any number of chemical entities, provided the end block prevents degradation of the molecule. In one embodiment, the end blocks are alkyl or O-alkyl, where the alkyl moiety can be straight chained, branched or cyclic but is preferably a straight chain containing 1-4 carbons. X and Z may be the same chemical moiety (e.g., butyl groups) or two different chemical moieties (e.g., Z is a butyl group and X is a butanol).

Preferred examples of such compounds have X or Z blocking groups, which independently comprise
CH₃CH₂CH₂CH₂—; CH₃CH₂CH₂—; CH₃CH₂—; HO—CH₂CH₂CH₂CH₂—; XO—CH₂CH₂CH₂CH₂—; or ZO—CH₂CH₂CH₂CH₂—.

A particularly preferred example of such compounds is the compound Nu-2 ((4-hydroxybutyl)-phosphate-5'-uridine-2'-methoxy-3'-phosphate-(4-hydroxybutyl)):

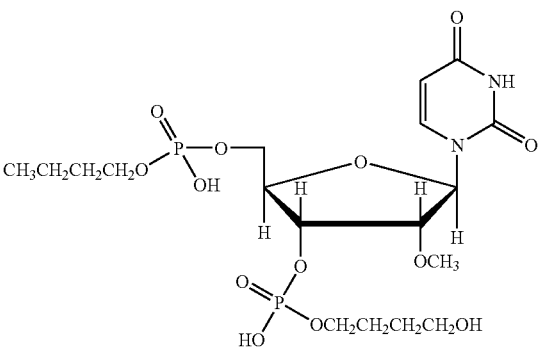

Nu-2

A further particularly preferred example of such compounds is the compound Nu-3 (butyl-phosphate-5'-thymidine-3'-phosphate-butyl):

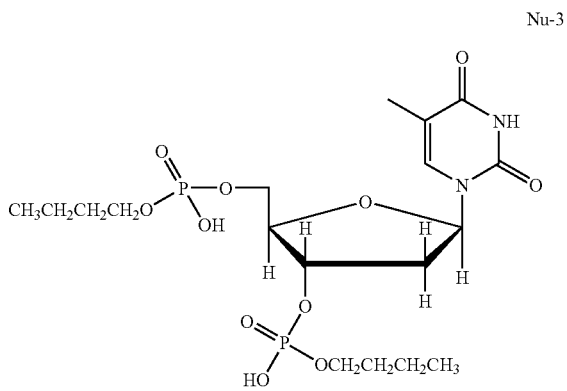

Nu-3

A further particularly preferred example of such compounds is the compound Nu-4 (butyl-phosphate-5'-ribose-3'-phosphate-butyl):

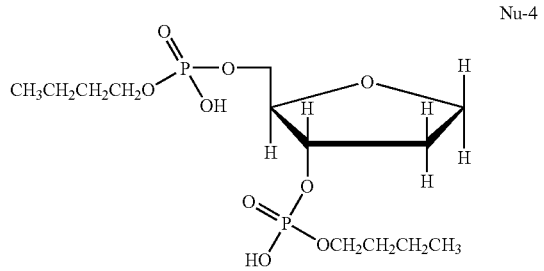

Nu-4

In one embodiment of the invention, the protonated compound has a sugar group, preferably either a ribose or a glucose group. The sugar structure of the molecules of the invention may be modified from that of a naturally occurring sugar, i.e. the overall structure of the sugar group is maintained, but one or more residues of the sugar is substituted and/or the sugar structure contains an additional residue compared to the unsubstituted form. See T. W. Graham Solomons, *Organic Chemistry*, J. Wiley and Sons, 6th edition (July 1998), pp. 937-971 for examples of sugar structures that may be used in the protonated compounds of the present invention.

Figure 4:
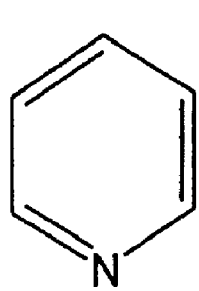
FIG. 4 illustrates exemplary single ring chemical moieties (W) that may be attached to a sugar group in the central group (Y) in the present invention.
Figure 4:
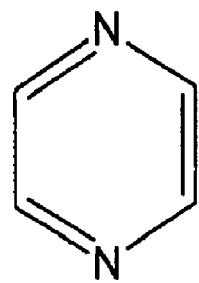
Figure 4:
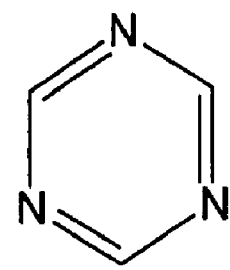
Figure 5:
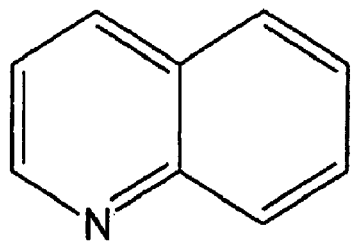
FIGS. 5 and 6 illustrate exemplary double and multiple ring chemical moieties (W) that may be attached to a sugar group in the central group (Y) in the present invention.
Figure 5:
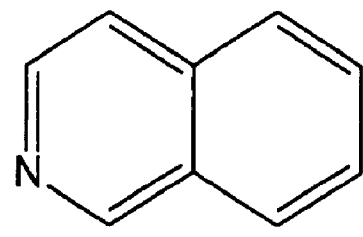
Figure 5:
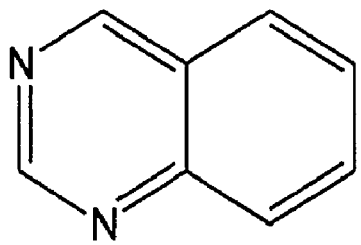
Figure 5:
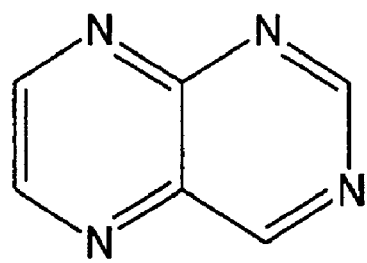
Figure 6:
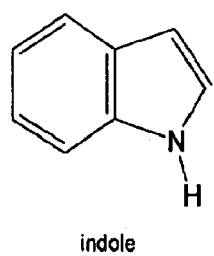
Figure 6:
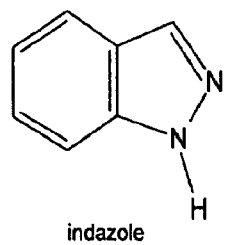
Figure 6:
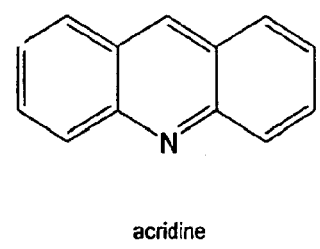
Figure 6:
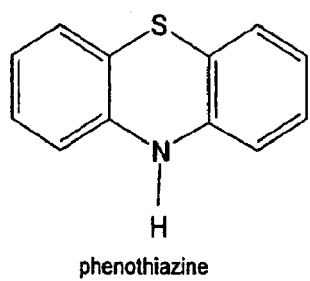
Figure 6:
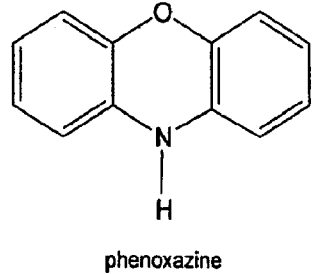
Figure 6:
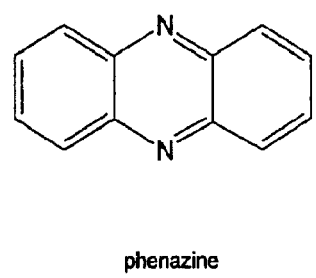
Figure 7:
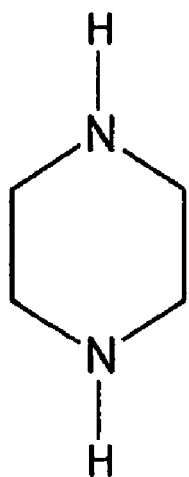
FIG. 7 illustrates exemplary partially or totally hydrogenated chemical moieties (W) that may be attached to a sugar group in the central group (Y) in the present invention.
Figure 7:
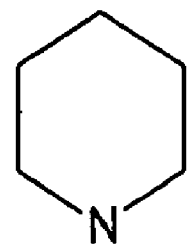
Figure 8:
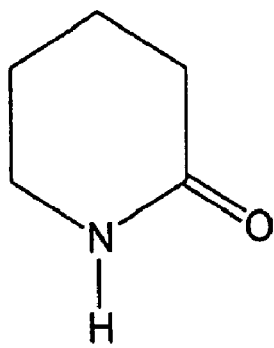
FIG. 8 illustrates an exemplary oxidized ring structure (W) that may be attached to a sugar group in the central group (Y) in the present invention.
Figure 9:
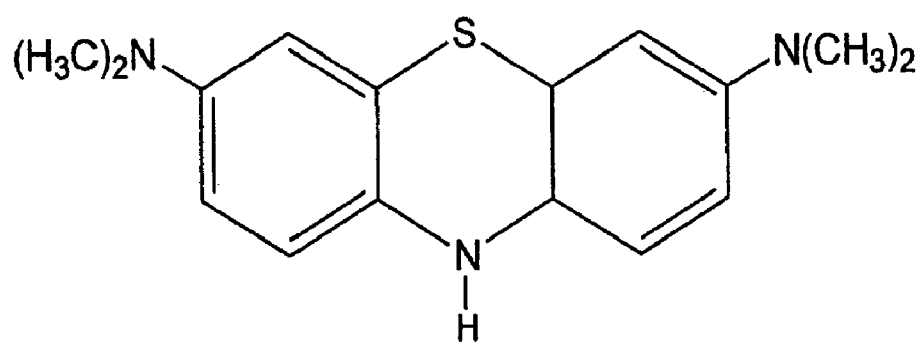
FIG. 9 illustrates an exemplary proton acceptor substituent (W) that may be attached to a sugar group in the central group (Y) in the present invention.

"W" as used in the structures and drawings of the present invention is a purine or pyrimidine, or a modified analogue of a purine or pyrimidine. FIGS. 4-8 illustrate exemplary substituent groups (W) that may be added to the naturally occurring structure of the sugar group for use in protonated compounds of the present invention. Such compounds (W) include, but are not limited to, modified analogues of purines and pyrimidines that do not form Watson-Crick base pairing with the naturally occurring bases, such as 2-aninoadenosine, theobromine, caffeine, theophylline, and uric acid; structures based on single ring structures such as pyridine, pyrazine, or triazine (FIG. 4):

structures based on multi-ring structures such as indole, acridine, indazole, phenoxazine, phenazine, phenothiazine, quinoline, isoquinoline, quinazoline, and pteridine (FIG. 5):

partially or totally hydrogenated single and multi-ring structures (FIG. 6):

partially oxidized single and multi-ring structures, e.g., caprolactam (FIG. 7):

structures with proton acceptor substituents, e.g. nitrogen-containing heterocyclics such as leucomethylene blue (FIG. 8):

and other structures that have similar electron configurations to purines and pyrimidines.

Each of these substituents may be further modified with electron withdrawing or donating groups, halogens, alcohols, diols, phosphorus amides, and phosphonic acids and the like to adjust the proton acceptance capability and/or other characteristic of the compound. Although the structure W is illustrated as being substituted at the 1 carbon site of the sugar molecule, the W structure may be linked to a different site, e.g., the 2 or 3 carbon site of the sugar group.

Substituents are in general selected to enhance one or more effects of the compound, e.g., to enhance pH, decrease toxicity and the like. Particular chemical moieties that are selected as central groups in the protonated compounds will be easily identified by one skilled in the art upon reading the present disclosure, and such moieties can be found in references such as T. W. Graham Solomons, *Organic Chemistry*, J. Wiley and Sons, 6th edition (July 1998); S. F. Sun, *Physical Chemistry of Macromolecules: Basic Principles and Issues* (1994); J. March, *Advanced Organic Chemistry: Reactions, Mechanisms, and Structure*, 4th edition (August 1992); and L. Stryer, *Biochemistry*, 4th edition (March 1995).

The compounds of the invention are synthesized using organic chemical synthetic methods known in the art. See, e.g., Example 7.

B. The Protonated Compounds of the Invention and Selected Physical Properties

1. Generation of the Protonated Compounds

Protonation of the compounds of the invention is the process by which protons (or positive hydrogen ions) are added to the reactive sites on the molecule. As the number of reactive sites that are protonated increases, the pH obtained when the compounds are dissolved in water having a pH of 7 decreases, and thus the amount of protonation of the compounds of the invention can be determined by measuring the pH of solutions of water after addition of the compounds of the present invention. Preferably, the compounds of the present invention are protonated so that when dissolved in water (pH 7), they form an aqueous solution having a pH of between less than pH 7 to about 1, preferably between less than about pH 6 to about 1, and more preferably between less than about pH 5 to about 1. In a more preferred embodiment, the compounds of the present invention are protonated so that when dissolved in water (pH 7), they form an aqueous solution having a pH of between less than about pH 4.5 to about 1, preferably between less than about pH 4 to about 1, more preferably between less than about pH 3 to about 1, and still more preferably less than about pH 2 to about 1. Specifically, the pH can be adjusted to be optimal for any given active agent by controlling the amount of protonation of the compound.

Protonated forms of the described compounds can be generated by subjecting the purified, partially purified, or crude compounds, to a low pH (e.g., acidic) environment. Purified or crude compounds were protonated with acid, including phosphoric acid, nitric acid, hydrochloric acid, and acetic acid.

Lyophilized or dried-down preparations of compounds to be used in bacterial experiments were dissolved in pyrogen-free, sterile, physiological saline (i.e., 0.85% saline), sterile Sigma water, and filtered through a 0.45 micron Gelman filter (or a sterile 0.2 micron pyrogen-free filter).

When suspended in water or saline, the compounds typically exhibited a pH between 1 and 4.5 depending upon the level of protonation/acidification, which is determined by how much acid is used in the acidification process.

Other procedures to prepare protonated compounds known to the skilled artisan are equally contemplated to be within the scope of the invention. Once the compounds of the present invention have been protonated, they may be separated from any undesired components like, for example, excess acid. The skilled artisan would know of many ways to separate the compounds from undesired components, including but not limited to using an $H^+$-cation exchanger (e.g., $H^+$-SCX). For example, the compound may be subjected to chromatography following protonation. In one embodiment, the compound is run over a poly(styrene-divinyl benzene) based resin (e.g., Hamilton's PRP-1 or 3 and Polymer Lab's PLRP) following protonation.

The protonated compounds can be used directly, or in a preferred embodiment, processed further to remove any excess acid and salt, e.g., via precipitation, reverse phase chromatography, diafiltration, or gel filtration. The protonated compounds can be concentrated by lyophilization, solvent evaporation, etc. When suspended in water or saline, the acidified compounds of the invention typically exhibit a pH of between 1 and 4.5 depending upon the level of protonation/acidification, which can be determined by how much acid is used in the acidification process. Alternatively, compounds can be protonated by passage over a cation exchange column charged with hydrogen ions.

2. Acid and Nuclease Resistance.

By introducing the modifications such as those described above to the compounds of the invention, the compounds are rendered more acid and nuclease resistant. Percent acid degradation may be determined using analytical HPLC to assess the loss of functional molecules, or by other suitable methods. Acid degradation is generally measured as a function of time. Preferably, the protonated compounds of the invention are also nuclease resistant, which allows these molecules to maintain activity (e.g., pH stability) in an in vivo setting. Percent degradation of the molecules in a setting containing nuclease may be determined by methods known to those skilled in the art, such as mass spectroscopy. Nuclease degradation is generally measured as a function of time. Preferably, a reference compound is employed in determining the extent or rate of acid or nuclease degradation. The compounds of the invention are 10%, 20%, 30%, 40%, 50%, 70%, 90%, 100%, 150%, 200%, 300%, 500%, 750%, or 100% more stable than a reference compound.

II. FORMULATIONS, DOSES, AND DOSING REGIMES

The invention further provides pharmaceutical and homeopathic compositions.

A. Pharmaceutical Compositions. As used herein, the term "pharmaceutical composition" refers to a therapeutic composition that is used to treat a particular disease or disorder or symptoms, and that is suitable for systemic, oral, topical or aerosol administration in humans and in animals. The presently described antimicrobial and antiviral compositions may be administered to the body by any suitable means used to administer conventional antibiotics, antifungals, and antivirals. For example, the compositions may be administered via oral, injection, topical or aerosol routes.

1. Formulations.

The Compositions containing the compounds of the invention in admixture with one or more pharmaceutically acceptable excipients can be prepared according to known techniques. The excipient may take a wide variety of forms depending on the form of preparation desired for administration, e.g. intravenous, oral, topical, transdermal, aerosol (for topical or inhalation therapy), suppository, parenteral or spinal injection. The excipient may contain any number of carriers. In addition, the composition may contain stabilizers, preservatives, and other ingredients, in any useful amount, providing that they do not significantly adversely affect the ability of the pharmacological compositions to treat the physiological condition. It is well within the skill of one in the art to determine an appropriate mode of administration and to select an appropriate delivery system.

a. Topical: Additives in Topical Compositions of the Invention

A variety of topical delivery systems are well known in the art for delivering bioactive compounds to bacteria in an animal. These systems include, but are not limited to topical creams, solutions, suspensions, emulsions, nasal spray, aerosols for inhalation, and suppository administration. The specific topical delivery system used depends on the location of the bacteria, and it is well within the skill of one in the art to determine the location of the bacteria and to select an appropriate delivery system. Similar ranges of topical delivery systems are well known in the art for delivering the compounds of the invention to a site in an animal that is affected by either fungal or viral infections, and equivalently, the appropriate topical delivery system can be determined by one of skill in the art for a specific infection type. Some exemplary systems are described in the following paragraphs.

The protonated compounds of the invention may be used in conjunction with active agents in products such as lotions, creams, and topical solutions. Other compounds may also be added to have additional moisturizing effects and to improve the consistency of the composition. Examples of such compounds include, but are not limited to: cetyl esters wax, stearyl alcohol, cetyl alcohol, glycerin, methyl paraben, propyl paraben, quaternium-15, humectants, volatile methylsiloxane fluids, and polydiorganosiloxane-polyoxyalkylene. See, e.g., U.S. Pat. Nos. 5,153,230 and 4,421,769, which are both incorporated herein by reference. If it is desirable for the composition to have additional cleaning effects, chemicals such as sodium lauryl sulfate or a metal salt of a carboxylic acid may be added.

A wide variety of nonvolatile emollients are useful herein, non-limiting examples of which are listed in McCutcheon's, Vol. 2 *Functional Materials*, North American Edition, (1992), pp. 137-168, which is incorporated herein by reference in its entirety, and *CTFA Cosmetic Ingredient Handbook*, Second Edition (1992) which lists Skin-Conditioning Agents at pp. 572-575 and Skin Protectants at p. 580, which is also incorporated herein by reference in its entirety.

Among the nonvolatile emollient materials useful herein especially preferred are silicones, hydrocarbons, esters and mixtures thereof.

Examples of silicone emollients include polyalkylsiloxanes, cyclic polyalkylsiloxanes, and polyalkylarylsiloxanes. Suitable commercially available polyalkylsiloxanes include the polydimethylsiloxanes, which are also known as dimethicones, non-limiting examples of which include the Vicasil™ series sold by General Electric Company and the Dow Corning™ 200 series sold by Dow Corning Corporation. Commercially available polyalkylsiloxanes include cyclomethicones (Dow Corning™ 244 fluid), Dow Corning™ 344 fluid, Dow Corning™ 245 fluid and Dow Corning™ 345), etc. A suitable commercially available trimethylsiloxysilicate is sold as a mixture with dimethicone as Dow Corning™ 593 fluid. Also useful herein are dimethiconols, which are hydroxy terminated dimethyl silicones. Suitable commercially available dimethiconols are typically sold as mixtures with dimethicone or cyclomethicone (e.g., Dow Corning™ 1401, 1402, and 1403 fluids). Suitable commercially available polyalkylarylsiloxanes SF1075 methylphenyl fluid (sold by General Electric Company) and 556 Cosmetic Grade phenyl trimethicone fluid (sold by Dow Corning Corporation).

Hydrocarbons useful herein include straight and branched chain hydrocarbons having from about 10 to about 30 carbon atoms, more preferably from about 12 to about 24 carbon atoms, and most preferably from about 16 to about 22 carbon atoms. Non-limiting examples of these hydrocarbon materials include dodecane, squalane, cholesterol, 5 hydrogenated polyisobutylene, docosane (i.e., a $C_{22}$ hydrocarbon), hexadecane, isohexadecane (a commercially available hydrocarbon sold as Permethyl™ 101A by Presperse, South Plainsfield, N.J.). Other hydrocarbon materials useful herein include paraffins and mineral oils such as USP light mineral oil (e.g., Klearol™ available from Witco Corp., Melrose Park, Ill.) and USP heavy mineral oil (e.g., Klearol™ available from Witco Corp., Melrose Park, Ill.).

The compositions of the invention may include propylene glycol. Propylene glycol acts as a surfactant and assists in penetration, contact, and absorption of the active ingredients. Propylene glycol also serves as a preservative. The compositions of the invention may also include a non-ionic surfactant, such as polysorbate. Such a surfactant provides better surface contact of the composition with the vaginal mucosa by further reducing surface tension.

Suppositories are prepared by mixing the protonated compounds with a lipid vehicle such as theobroma oil, cacao butter, glycerin, gelatin, or polyoxyethylene glycols.

Also useful as nonvolatile emollients are esters, including esters of monofunctional and difunctional fatty acids that have been esterified with alcohols and polyols (i.e., alcohols having two or more hydroxy groups). A wide variety of esters are useful herein, with long chain esters of long chain fatty acids being preferred (i.e., C10-40 fatty acids esterified with C10-40 fatty alcohols). Non-limiting examples of esters useful herein include those selected from the group consisting of diisopropyl adipate, isopropyl myristate, isopropyl palmitate, myristyl propionate, ethylene glycol distearate, 2-ethylhexyl palmitate, isodecyl neopentanoate $C_{12-15}$ alcohols benzoate, di-2-ethylhexyl maleate, ceryl palmitate, myristyl myristate, stearyl stearate, cetyl stearate, behenyl behenrate, and mixtures thereof.

Certain additives, such as aliphatic alcohols, have limited solubility's in aqueous solution. Compositions comprising any of these compounds$_1$ optionally may be formulated, with a lipophilic phase, as in emulsions and liposome dispersions and formulations. Liposomal formulations offer distinct advantages in extending circulation time of the compound, permeability of the compounds and in overall efficacy as antibacterials, antifungals, and antivirals. For example, the active agent may be combined with a lipid, cationic lipid, or anionic lipid (which may be preferred for protonated compounds and/or acidic active agents, e.g., salicylic acid). The resulting emulsion or liposomal suspension in conjunction with the pH stabilizing qualities of the compound of the invention can effectively increase the in vivo half-life of the activity of the composition. Examples of suitable anionic lipids for use with compositions of the invention include, but are not limited to, cardiolipin, dimyristoyl, dipalmitoyl, or dioleoyl phosphatidyl choline or phosphatidyl glycerol, palmitoyloleoyl phosphatidyl choline or phosphatidyl glycerol, phosphatidic acid, lysophosphatidic acid, phosphatidyl serine, phosphatidyl inositol, and anionic forms of cholesterol. The use of cationic, anionic, and/or neutral lipid compositions or liposomes is generally described in International Publications Nos. WO 90/14074, WO 91/16024, WO 91/17424, and U.S. Pat. No. 4,897,355, herein incorporated by reference.

In one aspect of the invention, the compounds of the invention are incorporated into liposomes. In some embodiments of the invention, neutral lipids, cholesterol, and/or polyethylene glycol (PEG) are utilized in the liposomes. In some embodiments the liposomal composition is composed of partially hydrogenated soy phosphatidylcholine (PHSC), cholesterol, methoxy-terminated PEG (mPEG), and/or distearoyl phosphatidyl ethanolamine (DSPE). In some embodiments the ratio of PHSC:mPEG:DSPE may be in the range of about 40:50:10 w/w % to about 60:30:10 w/w % or to about 60:35:5 w/w %. In some embodiments the percentage of PHSC is in the range of about 40% to about, 60 w/w % of the total lipid content. In some embodiments the percentage of mPEG is in the range of about 25% to about 45 w/w % of the total lipid content. In some embodiments the percentage of DSPE is in the range of about 3% to about 15 w/w % of the total lipid content. In other embodiments, the liposome formulation comprises of partially hydrogenated soy phosphatidylcholine (PHSC), cholesterol, and methoxy-terminated PEG (mnPEG). In some embodiments the ratio of PHSC:cholesterol:mPEG may be in the range of about 40% to about 60 w/w % PHSC, about 30% to about 40 w/w % cholesterol, and about 5% to about 10 w/w % mPEG. In some other embodiments, the liposome formulation comprises about 56% PHSC, about 38% cholesterol and about 6% MPEG. The liposomes can be prepared in any method known in the art. In some embodiments, an ethanol injection method is used to produce liposomes for use in compositions of the invention.

In some embodiments of the invention, the liposomes have a particle size of about 60 nm to about 120 nm diameter. In other embodiments of the invention, the liposomes have a particle size of about 75 nm to 110 nm, or about 80 nm to about 100 nm.

The ratio of a compound of the invention to lipids in the liposomal composition may be about 1:9 w/w to about 1:3 w/w. In some embodiments the ratio of a compound of the invention to lipids in the liposomal composition may be about 1:5 w/w to about 1:3 w/w.

For external application to intact skin or for disinfection of nonliving surfaces, an organic solvent or cosolvent such as ethanol or propanol may be employed. Evaporation of the solvent leaves a residue of the antibiotic and protonated compound on the treated surface to inhibit reinfection.

Any of the above described compositions may further be used in transdermal modes of application.

b. Aerosol Compositions.

Aerosols (e.g. for intranasal or mucosal administration) can be prepared by dissolving or suspending the protonated compounds and an active agent in a propellant such as ethyl alcohol or in propellant and solvent phases. The pharmaceutical compositions for topical or inhalation therapy will generally contain from about 0.01% by weight (of the protonated compounds) to about 40% by weight, preferably about 0.02% to about 10% by weight, and more preferably about 0.05% to about 5% by weight depending on the particular form employed.

c. Oral Compositions.

C. In preparing the compositions in oral dosage form, any of the usual pharmaceutical media may be employed such as, for example, water, glycols, oils, alcohols, flavoring agents, preservatives, coloring agents, and the like in the case of oral liquid preparations (such as for example, suspensions, elixirs, and solutions); or carriers such as starches, sugars, diluents, granulating agents, lubricants, binders, disintegrating agents and the like in the case of oral solid preparations (such as for example, powders, capsules, and tablets).

d. Injectable Compositions.

For administration by injection, preparations may comprise an aqueous solution of a water soluble, or solubilized, and pharmacologically acceptable form of the compound of the invention in an appropriate liquid, e.g., water or saline solution. Injectable suspensions may also be prepared using appropriate liquid carriers, suspending agents, agents for adjusting the isotonicity, preserving agents, and the like. Actual methods for preparing administrable pharmacological compositions and adjustments necessary for administration to mammals will be known or apparent to those skilled in the art.

Particular formulations may be manufactured according to methods well known in the art. Formulations are given in, for example, Remington's Pharmaceutical Sciences and similar reference works.

2. Doses and Dosing Regimes

The presently described compounds may be formulated with a variety of active ingredients and a variety of physiological carrier molecules. The compounds may optionally be complexed with molecules that enhance their ability to enter the target cells. Examples of such molecules include, but are not limited to, carbohydrates, polyamines, amino acids, peptides, lipids, and molecules vital to bacterial growth.

Administration of the composition will introduce the compounds of the invention to the mammal in a diluted amount. Exemplary unit dosages for oral, injectable, aerosol, or topical administration may be more than about 0.01, 0.05, 0.1, 0.5, 1, or 5 mg/kg, and/or less than about 10, 5, 1, 0.5, 0.1, or 0.05 mg/kg. Exemplary unit dosage ranges may be between about 0.01 mg/kg and 10 mg/kg, or between about 0.010 mg/kg and 1.0 mg/kg, or between about 0.10 mg/kg an 1.0 mg/kg. In some embodiments, the compositions of the invention are administered at unit dosages of about 0.01 to about 100 ug per kg of body weight, or about 0.1 to about 100 ug per kg of body weight, or about 0.1 to about 10 ug per kg of body weight, or about 1 to about 10 ug per kg of body weight, or about 1 to about 5 ug per kg of body weight. In some embodiments, unit dosages of the composition of the invention are at or below 100 ug per kg of body weight, or at or below 10 ug per kg of body weight, or at or below 1 ug per kg of body weight, or at or below 0.1 ug per kg of body weight, or at or below 0.01 ug per kg of body weight.

When orally administered, one dosage unit may be administered once every 10, 9, 8, 7, 6, 5, 4, 3, 2, or one day, or 1, 2, 3, 4, 5, 6, 7, 8, 9, 10, or more than 10 times per day until relief is achieved or until the symptoms disappear or are satisfactorily attenuated. In some embodiments, one dosage unit is administered about once to about four times per day. In some embodiments, a patient is instructed to orally take two to three dosage units per day. The dosage unit may be placed under the tongue of the patient or simply swallowed for such oral administration.

The pharmaceutical compositions for topical or aerosol form may contain from about 0.001 percent by weight (of the compound of the invention) to about 40 percent by weight, preferably about 0.02 percent to about 10 percent by weight, and more preferably about 0.05 percent to about 5 percent by weight depending on the particular form employed.

When topically administered, one dosage unit may be administered once every 10, 9, 8, 7, 6, 5, 4, 3, 2, or one day, or 1, 2, 3, 4, 5, 6, 7, 8, 9, 10, or more than 10 times per day until relief is achieved or until the symptoms disappear or are satisfactorily attenuated. In some embodiments, one dosage unit is administered about once to about four times per day.

When administered via aerosol, one dosage unit may be administered once every 10, 9, 8, 7, 6, 5, 4, 3, 2, or one day or 1, 2, 3, 4, 5, 6, 7, 8, 9, 10, or more than 10 times per day until relief is achieved or until the symptoms disappear or are satisfactorily attenuated. In some embodiments, one dosage unit is administered about once to about four times per day.

When administered via injection, one dosage unit may be administered once every 10, 9, 8, 7, 6, 5, 4, 3, 2, or one day, or 1, 2, 3, 4, 5, 6, 7, 8, 9, 10, or more than 10 times per day until relief is achieved or until the symptoms disappear or are satisfactorily attenuated. In some embodiments, one dosage unit is administered about once to about four times per day.

B. Homeopathic compositions In some embodiments, the invention provides homeopathic compositions. Homeopathic compositions may be made by methods known in the art. One exemplary method of making a homeopathic composition comprises (i) triturating solid compound of the invention in a 1/9 ratio with lactose to produce a 1× solid and (ii) repeating the process until the desired attenuation is achieved. In a related vein, a method of making a homeopathic composition comprising (i) dissolving 1 part compound of the invention by weight in liquid to produce ten volumes of liquid attenuation labeled 1× and optionally (ii) mixing 1 ml of the 1× attenuation with 9 ml of diluent to produce a lower concentration, is also addressed.

In some embodiments, the invention includes homeopathic compositions containing compounds of the invention. In one embodiment, tablets for homeopathic use are preferably produced as placebo tablets that are then medicated by dripping or spraying liquid potencies onto the tablets in such a manner as to ensure a coefficient of impregnation of almost 100 percent. The placebo tablets are preferably formed by compression. Pills or granules are preferably spherical in shape, of about 4 millimeters diameter and 3 to 5 centigrams in weight. They are preferably prepared (from pure lactose) and medicated in the same manner as tablets. For example, solid compound of the invention can be triturated (i.e., ground up) in a 1/9 ratio with lactose (1 gram of oligonucleotide+9 grams of lactose) to produce a 1× solid. The process is repeated (1 gram of that material plus 9 grams of lactose) until the desired attenuation is achieved.

For homeopathic compositions, the excipient may contain any number of carriers, and preferably homeopathic carriers, e.g., homeopathic agents that may increase the efficacy of the homeopathic composition or help to alleviate symptoms associated with a physiological condition. For example, compounds can be dissolved in a liquid 1 part by weight to produce a tenfold volume liquid attenuation labeled 1×. To produce lower dilutions 1 ml of the 1× attenuation is used (mixed thoroughly) with 9 ml of diluent to produce 2×. This process is repeated until the desired attenuation is achieved. A homeopathic carrier solution such as that described in U.S.

Pat. No. 5,603,915 may be used for increasing the efficacy of the homeopathic agent. This carrier solution is sequentially subjected to an alternating current electrical treatment and a direct current electrical treatment, after which additional ingredients such as seawater, brain hormones, and biologically active enzymes are added. The electrical treatment of the carrier, along with the addition of homeopathically active substances, can be used to increase the efficacy of the homeopathic composition.

Alternatively, an electromagnetic carrier, such as described in U.S. Pat. No. 5,830,140 may be employed. For homeopathic preparations for example, compounds can be dissolved in a liquid 1 part by weight to produce a ten volumes of liquid attenuation labeled 1×. To produce lower dilutions 1 ml of the 1× attenuation is used (mixed thoroughly) with 9 ml of diluent to produce 2×. This process is repeated until the desired attenuation is achieved. Typical homeopathic unit doses are given in Table 1.

TABLE 1

Homeopathic Dosages of the Compounds of the Invention.

| Dilution/Potency | µg/kg |
|---|---|
| 2× | 50 |
| 3× | 5 |
| 4× | 0.5 |
| 5× | 0.05 |
| 6× | 0.005 |

When orally administered, one dosage unit may be administered once every 10, 9, 8, 7, 6, 5, 4, 3, 2, or one day, or 1, 2, 3, 4, 5, 6, 7, 8, 9, 10, or more than 10 times per day until relief is achieved or until the symptoms disappear or are satisfactorily attenuated. In some embodiments, one dosage unit is administered about once to about four times per day. In some embodiments, a patient is instructed to orally take two to three dosage units per day. The dosage unit may be placed under the tongue of the patient or simply swallowed for such oral administration.

When topically administered, one dosage unit may be administered once every 10, 9, 8, 7, 6, 5, 4, 3, 2, or one day, or 1, 2, 3, 4, 5, 6, 7, 8, 9, 10, or more than 10 times per day until relief is achieved or until the symptoms disappear or are satisfactorily attenuated. In some embodiments, one dosage unit is administered about once to about four times per day.

When administered via aerosol, one dosage unit may be administered once every 10, 9, 8, 7, 6, 5, 4, 3, 2, or one day, or 1, 2, 3, 4, 5, 6, 7, 8, 9, 10, or more than 10 times per day until relief is achieved or until the symptoms disappear or are satisfactorily attenuated. In some embodiments, one dosage unit is administered about once to about four times per day.

III. METHODS OF THE INVENTION

A. Therapeutic Use of Compositions Containing Protonated Compounds

Preferably, animal hosts that may be treated using the compositions of the present invention include, but are not limited to, invertebrates, vertebrates, birds, mammals such as pigs, goats, sheep, cows, dogs, cats, and particularly humans. The presently described compositions are also contemplated to be effective in combating bacterial contamination of laboratory cultures, consumables (food or beverage preparations), medical devices, hospital apparatus, or industrial processes.

Examples of bacterial organisms against which the methods and compositions of the invention are effective include gram positive bacteria, gram negative bacteria, and acid fast bacteria, and particularly, *Staphylococcus aureus, Streptococcus pyogenes, Streptococcus pneumoniae, Mycobacterium* and *Escherichia coli*. The methods and compositions of the invention are effective against infection by all bacterial organisms, including members of the following genera: *Aerococcus, Listeria, Streptomyces, Chlamydia, Lactobacillus, Eubacterium, Arachnid, Mycobacterium, Peptostreptococcus, Staphylococcus, Corynebacterium, Erysipelothrix, Dermatophilus, Rhodococcus, Pseudomonas, Streptococcus, Bacillus, Peptococcus, Pneumococcus, Micrococcus, Neisseria, Klebsiella, Kurthia, Nocardia, Serratia, Rothia, Escherichia, Propionibacterium, Actinomyces, Helicobacter, Enterococcus, Shigella, Vibrio, Clostridium, Salmonella, Yersinia,* and *Haemophilus*.

A range of fungi or moulds, called dermnatophytes, cause fungal infections of the skin. These fungi are parasites on the skin and cause different symptoms in different parts of the body. They are very infectious and are passed from person to person. Although typically these infections are topical, in certain patients (e.g., immunosuppressed patients) they may occur systemically or in internally.

Fungal infections that may be treated with the compositions of the present invention include dermatophytosis (*Trichophyton, Epidermophyton*, and *Microsporum*), candidiasis (*Candida albicans* and other *Candida* species), tinea versicolor (*Pityrosporum orbiculare*), tinea pedea (*Trichophyton mentagrophytes, Trichophyton rubrum*, and *Epidermophytonfloccosum*), tinea capitis and ringworm (*Trichophyton tonsurans*).

Vaginal yeast infections are generally caused by *Candida albicans*, which, along with a few types of bacteria, are normally present in relatively small numbers in the vaginal area. Sometimes the yeast multiply rapidly and take over, causing candidiasis or monilia. This is often due to a change in the vaginal environment, injury, sexual transmission, HIV infection, etc. Common environmental disruptions that favor yeast include increased pH, increased heat and moisture, allergic reactions, elevated sugar levels, hormonal fluxes, and reductions in the populations of bacteria that are normally present.

Bactericidal and/or bacteriostatic activity of the compositions including compounds of the invention may be measured using any number of methods available to those skilled in the art. One example of such a method is measurement of antibacterial activity through use of a MIC (minimal inhibitory concentration) test that is recognized to be predictive of in vivo efficacy for the treatment of a bacterial infection with antibiotics. The compositions of the invention display antibacterial activity in this test, even without pretreatment of the bacteria to permeabilize the membrane.

The invention provides methods of inhibiting the growth of microorganisms by contacting the microorganisms with compositions of the invention in which the active agent is a protonated compound. These methods are effective against infections in vivo, and particularly topical infections. This is demonstrated by test data showing the minimum inhibitory concentrations (MIC) and minimum biocidal concentrations (MBC) of compositions against various pathogenic organisms cultured in vitro under standard conditions. These in vitro tests strongly correlate with in vivo activity, as is evidenced by the widespread use of the MIC and MBC determinations to predict utility of antimicrobial compositions in treatment of infection in animals, including humans.

Particularly striking is the ability of the present compositions comprising a protonated compound of the invention to extend the range of antimicrobial effectiveness against bacteria previously considered unreactive towards certain conventional antibiotics. For example, the protonated compounds of the invention may be especially useful in compositions to treat acne.

The protonated compounds of the invention, as well as having antibacterial activity, have activity as antifungals. The protonated compounds are thus useful as active agents for fungal infections such as tinea pedea and candidasis.

The protonated compounds of the invention, as well as having antibacterial activity, have activity as antivirals. The protonated compounds are thus useful as active agents for viral infections such as herpes simplex.

Compositions of the invention may be provided as topical disinfectants for sterilization of surfaces such as countertops, surgical instruments, bandages, and skin; as pharmaceutical compositions, including by way of example creams, lotions, ointments, or solutions for external application to skin and mucosal surfaces, including the cornea, dermal cuts and abrasions, burns, and sites of bacterial or fungal infection; as pharmaceutical compositions, including by way of example creams, lotions, ointments, emulsions, liposome dispersions or formulations, suppositories, or solutions, for administration to internal mucosal surfaces such as the oral cavity or vagina to inhibit the growth of bacteria or fungi, including yeasts; and as pharmaceutical compositions such as creams, gels, or ointments for coating indwelling catheters and similar implants which are susceptible to harboring bacterial or fungal infection.

1. Antimicrobials

The protonated compounds of the invention are useful as stabilizing and/or preservative compounds in topical antibiotic compositions, both prescription (e.g., benzomycin creams) and over-the-counter (e.g., anti-acne medications containing salicylic acid, benzoyl peroxide and the like.) When used in the therapeutic treatment of disease, an appropriate dosage of a composition containing the protonated compounds of the invention and an active ingredient may be determined by any of several well established methodologies. For instance, animal studies are commonly used to determine the maximal tolerable dose, or MTD, of bioactive agent per kilogram weight. In general, at least one of the animal species tested is mammalian. Those skilled in the art regularly extrapolate doses for efficacy and avoiding toxicity to other species, including human. Additionally, therapeutic dosages may also be altered depending upon factors such as the severity of infection, and the size or species of the host.

Where the therapeutic use of the presently described antimicrobial compositions is contemplated, the compositions are preferably administered by a pharmaceutically acceptable topical carrier. Typically, but not necessarily, the preferred formulation for a given antimicrobial composition is dependant on the location in a host where a given infectious organism would be expected to initially invade, or where a given infectious organism would be expected to colonize or concentrate. For example, topical infections are preferably treated or prevented by formulations designed for application to specific body surfaces, e.g., skin, mucous membranes, etc. In such an embodiment, the composition containing the active ingredient and the protonated compound is formulated in a water, ethanol, and propylene glycol base for topical administration. Alternatively, where the targeted pathogen colonizes nasal passages, compositions suitable for intranasal administration can be formulated.

Given that bacterial and fungal infections are particularly problematic in immuno-compromised individuals, such as patients suffering from acquired immunodeficiency disease syndrome (AIDS), HTV-infected individuals, patients under-going chemotherapy or radiation therapy, or bone marrow transplantation, etc., an additional embodiment of the presently described invention is the use of the presently described antimicrobial protonated compounds as prophylactic agents to prevent and/or treat infection in immuno-compromised patients.

2. Antivirals

The said compounds are based on the natural structures of nucleosides that are synthesized via the optimized synthetic routes. The compounds are modified by some substitutions on the sugar and bases with the 5' and/or 3' blockers. The said compounds possess efficient antiviral activities, stability and low toxicity.

Without being limited by mechanism, it is thought that the compounds inhibit virus replication via three possible mechanisms: 1.) termination of the chain extension by incorporating the compounds into the DNA or RNA synthesis; 2.) inhibition of viral replication by binding to the replication enzymes; or 3.) inhibition of virally induced nucleotide reductases, leading to the imbalance of the cellular pool of nucleosides.

Viruses that may be treated by compositions of the invention include, but are not limited to, HIV, HSV, CMV, HBV, HCV and influenza virus.

B. Conjunctive Therapies

The protonated compounds can also be used in conjunction with conventional antimicrobial agents in compositions of the invention. The added activity of the active ingredients may provide for a more efficacious composition, and can provide multiple mechanisms by which the microbes are targeted. Pharmaceutical compositions containing the compounds of the invention in admixture with an active agent and a pharmaceutical carrier can be prepared according to conventional pharmaceutical compounding techniques.

For example, compositions for the treatment of acne may comprise the protonated compounds of the invention with salicylic acid, benzoyl peroxide, and/or sulfur. These amounts of these compounds in compositions of the invention can be determined by one skilled in the art, the effective amounts are well documented. See, C. Zouboulis (Editor) *Sebaceous Glands, Acne and Related Disorders: Basic and Clinical Research, Clinical Entities and Treatment* (1998). Such conjunctive therapy using the protonated compounds of the invention can increase the efficacy of compositions without having to increase the amounts of the agents currently available to consumers, e.g., the amount found in over-the-counter products. Such compositions are preferably aqueous, as oil-based compositions may exacerbate the acne condition.

The protonated compounds are-also useful in general antibiotic creams for external use, e.g., for application to the skin or eye. Again, the protonated compounds can be used as the sole active agent, or may be used in conjunctive therapy with other agents, including but not limited to triclosan, erythromycin, neomycin sulfate and gramicidin, polymixin, gentamicin, clindamycin, and other topical antibiotics. See e.g., Yoshihito Honda (Editor), *Topical Application of Antibiotics: Recent Advances in Ophthalmology* (1998), and the *Physicians Desk Reference* (1999).

OTC antifungal medications that may be additional active ingredients in the compositions of the invention include: Miconazole, Miconazole nitrate, Polynoxylin, Clotrimazole, Sulconazole nitrate, Econazole nitrate, Tolnaftate, Selenium sulphide, Tioconazole Presciptive antifungals include drugs such as allylamines, azoles, polyene macrolides, flucytosine, pseudomycins and griseofulvin. Exemplary antifungals include Amphotericin B, Fluconazole/Difluian, Flucytosine, Foscarnet, Itraconazole/Sporonex, Ketoconazble/Nitoral, and Nystatin 1. See also Elewski, *Cutaneous Fungal Infections,* 2nd Edition (1998) and Segal, *Pathogenic Yeasts and Yeast Infections* (1994), which are both incorporated by reference.

The topical compositions of the invention contain the protonated compounds as described, and may contain any of a number of additives that are themselves active ingredients, such as a retinoic acid, glycolic acid, lactic acid, α-hydroxy acids, keto-hydroxy acids, citric acid, glucuronic acid, galacturonic acid, glucuronolactone, gluconolactone, α-hydroxybutyric acid, α-hydroxyisobutyric acid, malic acid, pyruvic acid, β-phenyllactic acid, β-phenylpyruvic acid, saccharic acid, mandelic acid, tartaric acid, tartronic acid, β-hydroxybutyric acid, vitamin A palmitate (retinyl palmitate) and/or vitamin E acetate (tocopheryl acetate). Each of these is preferably present in an amount from about 0.5 wt % to about 20 wt %. In addition, a UV absorbing or blocking material, such as PABA, may be used.

Additional compositions in which the compound of the invention is efficacious include those found in U.S. Pat. No. 5,652,266, directed to combination of alpha-hydroxy acid, retinoid and salicylic acid; U.S. Pat. No. 5,843,998, directed to a composition containing alpha hydroxy acids and carbamide peroxide, either with or without salicylic acid; U.S. Pat. No. 5,153,230, which is directed to a formulation in which the major active ingredient is glycolic acid; U.S. Pat. No. 4,464,392, which is directed to a antimicrobial formulations containing glycolic acid derivatives; and U.S. Pat. No. 4,105,782, which describes numerous other similar active agents that may be used in the composition of the invention.

The compositions of the invention may also be used as a carrier material for and/or in combination with other medicines, such as spermicidal agents, anti-viral agents and anti-fungal agents, thereby further broadening the compositions medical efficacy. The composition of the present invention may also include a topical anesthetic such as lidocaine hydrochloride and topical steroids, such as corticosteroid, to provide relief from pain or itching during treatment.

C. Cosmetic Use of Protonated Compounds of the Invention

The protonated compounds of the invention may be used in cosmetic products such as lotions, creams, and topical solutions as an antimicrobial preservative. The protonated compounds retard and/or prevent the growth of numerous species of bacteria in a cosmetic formulation, such as in a lotion, and thus may be used as a preservative to prevent and/or retard growth of bacteria in the cosmetic preparation. The protonated compounds may be used in this capacity with any known cosmetic preparation, provided the composition of the preparation is sufficiently low in pH to retain protonation of the compound, i.e. 7.0 or below. The protonated compounds are present in an amount sufficient to have an antimicrobial effect, and preferably between 0.25 wt % and 10.0 wt %, more preferably between 0.5 wt %, and 5.0 wt %.

The cosmetic composition of the invention may also contain any of a number of additives that are active ingredients, such as a glycolic or alpha-hydroxy acids, vitamin A palmitate (retinyl palmitate) and/or vitamin E acetate (tocopheryl acetate). Each of these is preferably present in an amount from about 0.5 wt. % to about 5 wt %. In addition, a UV absorbing or blocking material, such as PABA, may be used.

Other compounds may also be added to have additional moisturizing effects and to improve the consistency of the composition. Examples of such compounds include, but are not limited to: cetyl esters wax, stearyl alcohol, cetyl alcohol, glycerin, methyl paraben, propyl paraben, quaternium-15, humectants, volatile methylsiloxane fluids, and polydiorganosiloxane-polyoxyalkylene. See, e.g., U.S. Pat. Nos. 5,153,230 and 4,421,769, which are both incorporated herein by reference. If it is desirable for the composition to have additional cleaning effects, chemicals such as sodium lauryl sulfate or a metal salt of a carboxylic acid may be added.

D. Use of Protonated Compounds in Disinfectants

The protonated compounds of the invention may also find use as disinfectants, and particularly as liquid disinfectant preparations having biostatic or preferably biocidal properties. The disinfectant solution contains at least a sufficient amount of protonated compounds of the invention, and may also contain other active ingredients with biostatic and/or biocidal properties. For example, the disinfectant may contain protonated compounds of the invention with a suitable concentration of a quaternary ammonium compound such as: dimethylbenzyldodecylammonium chloride, dimethylbenzyl decylammonium chloride, dimethylbenzyl decylammonium bromide, and dimethylbenzylloctylammonium chloride.

In another example, suitable microbiocidal biguanidine compounds, such as oligohexamethylene biguanide salts and bisbiguanides, can be used. See, e.g., U.S. Pat. No. 5,030,659, which is incorporated herein by reference. Additional biocidal ingredients include aldehydes, phenol derivatives, and halogen phenyl derivatives. See, e.g., U.S. Pat. No. 5,767,054, which is incorporated herein by reference. Other compounds with such activity, as will be recognized by those skilled in the art, may also be used in conjunction with the protonated compounds of the invention.

In addition to the described active components, the disinfectant preparations of the invention may contain other typical components depending on the desired use of the formulation. In particular, an acidifier may be used to keep the pH range of the disinfection solution below 6. Suitable solvents for the protonated compounds and/or the other active ingredients may be employed, and preferably are water or water miscible organic solvents. Solutions such as these may be readily sprayed using compressed air or any other propellants known by those in the art. By assembling the inactive (e.g., compounds of the invention) and/or other active (e.g., antibiotic) agents into lipid-associated structures, the compositions of the invention may be targeted to specific bacterial cell types by the incorporation of suitable targeting agents (i.e., specific antibodies or receptors) into the lipid complex.

These preparations of the invention are especially suitable for surface disinfection in medically-related environments, such as hospitals, veterinary clinics, dental and medical offices and the like. Use of solutions of the invention in the sterilization of surgical instruments is especially preferred. These preparations are also useful in public areas such as schools, public transport, restaurants, hotels and laundries. The disinfectants also find use in home as sanitizers for toilets, basins, and kitchen areas.

The protonated compounds of the invention may also be used in disinfection solutions for skin. Such compositions contain the protonated compound of the invention in a solution that is in a vehicle suitable for topical use. The disinfectant may be of the quick-drying variety, in which case it is desirable for the protonated compounds to be in an ethanol base. Such solutions preferably contain an emollient for the skin as well, since the alcohol tends to be extremely drying to skin. Examples of suitable emollients include, but are not limited to: a polyhydric alcohol such as polyethylene glycol, glycerin, diglycerin, propylene glycol, butylene glycol, erythritol, dipropylene glycol, and sorbitol. The amount of emollient may be in the range of 0.1-3.0 w/w %, and more preferably in the range 0.2-1.5 w/w %. In the case where the content of the emollient is less than 0.1% (by weight) it may not be very effective, and over 3.0%, the solution may be overly sticky.

Disinfectant solutions for the skin are especially useful in disinfection of hands following medical treatment or waste management. Disinfection may also be useful in surgical settings, both for the medical staff and to sterilize the area of surgery on the patient. For example, surgical instruments can be coated with the protonated compounds of the invention to provide for a sterile coating prior to surgery.

IV. EXAMPLES

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g., amounts, temperature, concentrations, etc.) but some experimental errors and deviations should be allowed for. Unless otherwise indicated, parts are parts by weight, molecular weight is average molecular weight, temperature is in degrees centigrade, and pressure is at or near atmospheric.

Example 1

Bacterial Growth Studies in a Burn Model

Burn wound infection in mice can be established by subcutaneous or topical administration of the bacteria to the sites of the burn. In order to demonstrate the anti-microbial activity of the compounds of the present invention, the ability of such compounds to prevent burn wound infection was studied.

Six-week old BALB/c female mice were obtained from the mouse breeding colony at DRES, with breeding pairs purchased from Charles River Canada Ltd. (St. Constant, Quebec, Canada). The use of animals described in this study was approved by DRES Animal Care Committee. Care and handling of animals described in this study followed guidelines set out the Canadian Council on Animal Care.

*Pseudomonas aeruginosa* (Strain Utah 4) was initially cultured on the tripticase soya broth, aliquotted and frozen at −70° C. Prior to use, aliquots were thawed and diluted serially in sterile PBS just prior to administration into animals. To ensure viability and virulence, aliquots of the bacteria were periodically re-amplified in tripticase soya broth and colonies determined on tripticase soya agar plates.

$LD_{50}$ values were determined using the method of Reed and Muench (*Amer. J. Hyg.* (1938) 27:493-497), and were found to be approximately $4 \times 10^8$ and $2 \times 10^9$ CFUs, respectively, for subcutaneous and topical routes of infection. For establishing the lethal doses of the bacteria for the systemic burn wound infection, groups of mice were anesthetized with ketamine/xylazine mixture (50 mg/kg each, given intramuscularly), their backs were then shaved using a clipper, razor and shaving cream. To induce burn in the back of these animals, a brass bar (10×10×100 mm) was heated in a boiling water for 15 min. The end of the heated bar was then applied on the shaved back of the mice for 45 sec. After a waiting period of 30 min, 50 μl of the bacterial inoculum (containing approx. $1 \times 10^{8-11}$ CFU of total bacteria) were then applied subcutaneously into the sites of the burn on the animal back. The mice were then allowed to recover, and were monitored daily for symptoms and deaths. Three days later, the mice were shaved and burns were induced as described above. The inoculum containing the same numbers of bacteria was then topically applied (100 μl) evenly on the sites of the burn, and a custom made "mouse jacket" was then put on the infection site, for at least 2 hrs. These mice; were then monitored daily for symptoms and deaths. These lethal dosages of the *P. aeruginosa* strain used were found to change during the course of this study due to possible decreases in bacterial viability and virulence during storage. As a result, these values were regularly re-checked and adjusted. For all treatment studies, approx. 5 $LD_{50}$ of the bacteria were used. The survival pattern of the mice infected with 5 $LD_{50}$ of the bacteria administered by these two routes of infection was similar. Both routes of administration resulted in eventual death of all mice in the test groups by day 3 post infection. All control unburned animals that received equivalent doses of bacteria by either subcutaneous or topical administration without the burn were asymptomatic and found to be completely resistant to the infection. In the mice that received the burn and infection, the $LD_{50}$ of the bacteria administered topically was approximately 5-fold higher than the subcutaneous route. Unless otherwise stated, all treatment studies described were carried out using subcutaneous route of infection. This route of administration was chosen for subsequent studies as it does not require pretreatment of the mice with cyclophosphamide at 3 days prior to infection, and that it causes a more systemic infection.

Mice treated as described above were provided with Nu-2, Nu-3, Nu-4 and Nu-5 by subcutaneous administration (200 μl of solution of approximately 12 mg/ml), and their survival was compared to control, untreated mice. The results of this study are shown in Table 2. The results indicate that the compounds of the present invention were effective in attenuating the incidence of infection of burn wounds.

TABLE 2

Efficacy Of The Compounds Of The Present Invention In Treating Burn Wound Infection

| Compound | # animals surviving total# tested | % Survival | p Value (expt vs. control) |
|---|---|---|---|
| Nu-2 | 3/5 | 60% | 0.0184 |
| Nu-3 | 4/5 | 80% | <0.01 |
| Nu-4 | 5/5 | 100% | <0.01 |
| Nu-5 | 4/5 | 80% | <0.01 |
| Control | 1/45 | 2% | — |

Example 2

Subcutaneous Treatment with a Protonated Monomer

To determine the effectiveness of protonated compounds for the treatment of burn wound infection, mice were subcutaneously infected with 5 $LD_{50}$ of *P. aeruginosa* as described above. Mice were then treated in the following manner. For treatment of systemic infection (infection by subcutaneous injection of the bacteria), mice were treated at 2 and 8 hrs post infection. Three groups of mice were treated with protonated Nu-3. Group 1 received a subcutaneous injection of 100 μl 35 mg/ml protonated monomer; Group 2 received a subcutaneous injection of 17.5 mg/ml protonated injection; and group three received no monomer. All (5 out of 5) treated Group 1 animals survived, 2/5 animals of group 2 survived, and no control animals survived the burn infection.

The bacterial load was determined using the blood and organs of experimental animals. Blood, spleens, livers and the burnt skins were aseptically removed. The blood (100 μl) was serially diluted in sterile PBS and 100 μl of the diluted blood was plated for growth in tripticase soya agar plates. For the organs, they were homogenized in 2 (spleens and skins) or 5 ml (livers) of sterile PBS using hand-held tissue grinder. The tissue homogenates were serially diluted in sterile PBS, and were then plated for growth in TSA, and the inoculated plates were incubated at 37EC overnight. The number of CFUs was then determined.

The animals receiving 35 mg/ml dosage had no detectable bacterial load in the spleen, liver or blood. Animals receiving the 17.5 mg/ml dosage had a lower bacterial load than the control, untreated animals by an order of magnitude: $1.6 \times 10^4$ versus $9 \times 10^2$ in spleen and $1.2 \times 10^4$ versus $1.9 \times 10^3$ in liver (treated versus untreated).

The survival rates of control and treated mice were compared using the Mann-Whitney unpaired nonparametric one-tailed test. These tests were performed using GraphPad Prism software program (version 2.0; Graph PAD Software, Inc., San Diego, Calif.). Differences were considered statistically significant at $p<0.05$.

The results of this experiment indicate that the compounds of the present invention were effective for the treatment of burn wound infections.

Example 3

Treatment of Tinea Pedis

A 75 year old male with diabetes presented with an acute case of tinea pedis. This infection had been treated with conventional antifungals for a period of over a month with little progress made in clearing up this fungal infection. Treatment of the site of tinea pedis was initiated using a topical solution of Nu-3 at a concentration of 31 $A_{260}$/ml. Treatment of the area continued once a day for three days. At the end of the three-day period, the infection appeared to be completely eradicated.

The results of this experiment indicate that the compounds of the present invention were effective for the treatment of tinea pedis.

Example 4

Antimicrobial Activity of Compound Nu-4

The antimicrobial activity of the compounds of the present invention was further demonstrated by incubating various microorganisms in the presence of Compound Nu-4 of the present invention. For such incubations, a stock solution of Nu-4 (12.7 mM) was diluted using 5 sequential 2-fold dilutions (0.5 ml of test substance in 0.5 ml of 10% Meuller-Hinto broth ("MHB"). To each well of a 96 well microtiter plate were added 150 μl of MHB, 30 μl of compound dilution, 20 μl of 10× bacteria to give an equivalent of about $10^6$ colony forming units ("cfu")/ml. Plates were incubated for 24 hours at appropriate temperature, and then scored for growth (NG=no growth; +, some growth; ++, fair amount of growth; +++, dense growth). The results of this experiment are presented in Table 3 below.

TABLE 3

Antimicrobial Activity of Compound Nu-4

| Strain | Microbial Growth at Compound Dilution | | | | | | |
| --- | --- | --- | --- | --- | --- | --- | --- |
| | Stock | 1 | 2 | 3 | 4 | 5 | Control |
| *Stapylococcus aureus* ATCC#6538 | NG | NG | NG | NG | +++ | +++ | +++ |
| *Pseudomonas aeruginosa* ATCC#9027 | NG | NG | NG | NG | +++ | +++ | +++ |
| *Salmonella choleraesuis* ATCC#6539 | NG | NG | NG | NG | NG | ++ | +++ |
| *Escherichia coli* ATCC#6539 | NG | NG | NG | NG | +++ | +++ | +++ |
| *Salmonella typhimirium* hisG46 | NG | NG | NG | ++ | +++ | +++ | +++ |
| *Bacillus subtilis* ATCC#9372 | NG | NG | NG | NG | +++ | +++ | +++ |
| *Serratia marcessens* ATCC# 13880 | NG | NG | NG | NG | +++ | +++ | +++ |
| *Stapylococcus aureus* ATCC#33592 (methicillin and gentamycin resistant) | NG | NG | NG | NG | NG | +++ | +++ |
| *Candida albicans* ATCC01023 1 | NG | NG | ++ | +++ | +++ | +++ | +++ |
| *Enterococcus faecalis* ATCC 51575 (high level vancomycin resistant) | NG | NG | NG | NG | +++ | +++ | +++ |
| *Enterococcus faecalis* ATCC 51299 (low level vancomycin resistant) | NG | NG | NG | NG | +++ | +++ | +++ |
| *Stapylococcus aureus* SU (methicillin resistant) | NG | NG | NG | +++ | +++ | +++ | +++ |

The results of this experiment indicate that the compounds of the present invention possess broad antimicrobial activity.

Example 5

Antimicrobial Activity of Compound Nu-5

The antimicrobial activity of the compounds of the present invention was further demonstrated by incubating various microorganisms in the presence of Compound Nu-5 of the present invention. Such incubations were conducted as described in Example 4, except that a stock solution of Nu-5 (12.7 mM) was employed. Plates were incubated for 24 hours at appropriate temperature, and then scored for growth (NG=no growth; +, some growth; −++, fair amount of growth; +++, dense growth). The results of this experiment are presented in Table 4 below.

TABLE 4

Antimicrobial Activity of Compound Nu-5

| Strain | Microbial Growth at Compound Dilution | | | | | | |
|---|---|---|---|---|---|---|---|
| | Stock | 1 | 2 | 3 | 4 | 5 | Control |
| Stapylococcus aureus ATCC#6538 | NG | NG | NG | NG | +++ | +++ | +++ |
| Pseudomonas aeruginosa ATCC#9027 | NG | NG | NG | NG | +++ | +++ | +++ |
| Salmonella choleraesuis ATCC//6539 | NG | NG | NG | NG | NG | +++ | +++ |
| Escherichia coli ATCC#6539 | NG | NG | NG | NG | +++ | +++ | +++ |
| Salmonella typhimirium hisG46 | NG | NG | NG | +++ | +++ | +++ | +++ |
| Bacillus subtilis ATCC#9372 | NG | NG | NG | NG | +++ | +++ | +++ |
| Serratia marcessens ATCC#13880 | NG | NG | NG | +++ | +++ | +++ | +++ |
| Stapylococcus aureus ATCC#33592 (methicillin and gentamycin resistant) | NG | NG | NG | NG | +++ | +++ | +++ |
| Candida albicans ATCC#1023 1 | NG | NG | NG | NG | +++ | +++ | +++ |
| Enterococcus faecalis ATCC 51575 (high level vancomycin resistant) | NG | NG | NG | NG | ++ | +++ | +++ |
| Enterococcus faecalis ATCC 51299 (low level vancomycin resistant) | NG | NG | NG | NG | NG | +++ | +++ |
| Stapylococcus aureus SU (methicillin resistant) | NG | NG | NG | NG | +++ | +++ | +++ |

The results of this experiment also indicate that the compounds of the present invention possess broad antimicrobial activity.

Example 6

MIC Experiments with 3 Yeast Organisms: Antimicrobial Activity of Compounds Nu-3 and Nu-5

The antimicrobial activity of the compounds of the present invention was further demonstrated by incubating three yeast organisms in the presence of Compounds Nu-3 and Nu-5 of the present invention. For such incubations, stock solutions of Nu-3 (54 $A_{260}$/ml) and Nu-5 (12.7 mM) were diluted using 5 sequential 2-fold dilutions (30 μl of test substance in 30 μl of sterile water) for each organism. To each well of a 24 well microtiter plate were added 30 μl of each compound (dilutions were prepared directly in each well), 20 μl of 10× yeast cells to give an equivalent of about $10^6$ colony forming units ("cfu")/ml and 150 μl of 10% Sabouraud dextrose broth. Plates were incubated for 24 hours at 25° C. with shaking (200 RPM) with additional incubation at room temperature for 24 hours, and then scored for growth (NG=no growth; +, some growth; ++, fair amount of growth; +++, dense growth, ND=not done). The results of this experiment are presented in Table 5 below, and indicate that the compounds of the present invention possess broad antimicrobial activity against both prokaryotes and eukaryotes.

TABLE 5

Anti-Yeast Activity of Compounds Nu-3 and Nu-5

| Strain | Microbial Growth at Compound Dilution | | | | | | |
|---|---|---|---|---|---|---|---|
| | Stock | 1 | 2 | 3 | 4 | 5 | Control |
| | Compound NU-3 | | | | | | |
| Candida albicans ATCC#44374 | ND | NG | + | +++ | +++ | +++ | +++ |
| Candida albicans ATCC#44373 | ND | NG | + | +++ | +++ | +++ | +++ |
| Saccharomyces pastorianus ATCC#2366 | ND | NG | NG | NG | NG | +? | +++ |
| | Compound NU-5 | | | | | | |
| Candida albicans ATCC#44374 | ND | NG | + | ++ | +++ | +++ | +++ |
| Candida albicans ATCC#44373 | ND | NG | + | +++ | +++ | +++ | +++ |
| Saccharomyces pastorianus ATCC#2366 | ND | NG | NG | NG | NG | +? | +++ |

Example 7

Chemical Synthesis of Nu-3 Compound (Thymidine 3',5'-bis-(N-butylphosphate)

Thymidine (5.6 g) is concentrated from anhydrous acetonitrile to form a solid which is suspended in 85 ml of anhydrous dichloromethane. N-butylcyanoethyl-N,N-diisopropylphosphoramidite (12.67 gm) is added to the suspension using dichloromethane to transfer. The suspension is stirred vigorously and tetrazole (3.32 g) is added. The reaction is stirred overnight. The progress of the reaction is monitored by 1.) HPLC using a Zorbax C-8 column and an isocratic mobile phase of 75% acetonitrile in 0.1 M TEAA buffer at pH7.0, a flow rate of 1 ml/min, with detection at 254 nM to determine when less than 2% thymidine still remains, with appearance of a product peak at an elution time of 2.4 min. or 2.) $^{31}$P NMR spectroscopy to determine disappearance of amidite starting material. The reaction is cooled in a salt/ice bath to less than −10° C. A 5-6 M solution of t-butylhydroperoxide in decane (10 ml) is added dropwise from a pressure equalizing funnel. Stirring is continued and the reaction is allowed to come to room temperature. The progress of the reaction is followed by HLPC as above, and completion is observed in 2-3 hrs with the product peak appearing at an elution time of 1.5 min. The reaction solution is then washed successively with 5% sodium bisulfite, and saturated sodium chloride solution. The organic layer is separated and dried over anhydrous sodium sulfate, filtered, and concentrated to remove dichloromethane. The remaining decane containing residual oil is washed with diethyl ether, and the upper ethereal layer is carefully decanted away from the lower layer. The residual oil is dissolved in dichloromethane and diethyl ether is added. The oil is allowed to settle for approximately 15 min and the ethereal solvent is decanted. The remaining oil is dried under high vacuum overnight. The oily product is accurately weighed, dissolved in 10 ml of methanol per gm of oil, and 2 equivalents of 1N sodium hydroxide is added. Stirring is maintained at room temperature. The hydrolysis reaction is monitored by HPLC as above, the product is observed to elute at 1.2 min, and completion is observed within 1-2 hrs. The reaction mixture is concentrated under vacuum, with addition of dry methanol to co-evaporate the residual water away from the product. The resultant gum is triturated with acetonitrile (100 ml) and stirred for 1-2 hours until the gum precipitates as a filterable solid. The white solid is filtered, washed with acetonitrile, and dried under vacuum. The purity of the product (>99%) is evaluated by $^{31}$P and $^{1}$H NMR spectroscopy. Synthesis via this method is suitable for gram to kilo scale production.

Example 8

Protonation of Nu-3

0.1 N HCl is added to an aqueous solution of Nu-3 (100–300 A260 units/ml) until the solution has a pH of about 1. After acidification, the solution is passed through an acid-resistant column (Biorad or P4) to remove the residual acid and salt and the eluent is lyophilized. When the lyophilized product is dissolved in water or saline, the Nu-3 solution has a pH in the range of about 1.

Example 9

Preparation of Liposome Encapsulated Nu-3

A solution is made using PHSPC, cholesterol, and mPEG-DSPE in a ratio of 56:38:6 w/w with a total lipid concentration of 150 mM in ethanol, stirring until complete solution is achieved. This solution is added slowly to a solution of Nu-3 (50 mg/ml) in ethanol using vortex mixing, to a final ratio of lipid solution to Nu-3 solution of 1:2 (v/v). The mixture is passed through a membrane under pressure to form liposomes. The resulting liposomal mixture is sonicated for 20 sec and cycles through 5 min freeze/5 min thaw cycles for a total of four cycles. The liposomal mixture is dialyzed against PBS to remove ethanol, then is passed through a Sepharose column to separate unincorporated drug from the liposomal preparation of Nu-3. The resultant liposomal formulation of Nu-3 yields a particle size of 60-100 nm, and a drug to lipid ratio of 1:4 w/w.

Example 10

Determination of Antibacterial Effect of Nu-3

The efficacy of pulmonary delivery of liposomal Nu-3 is tested by examining the ability to inhibit growth of *P. aeruginosa* in rats. After anesthetization with Ketamine (90 mg/kg) and Xylazine (10 mg/kg), the rats are infected with $1 \times 10^7$ CFU of *P. aeruginosa*. A liposomal formulation of Nu-3 is administrated to rats intra-tracheally at a dose of 200A$_{260}$ units per rat. Fours days later, the rats are sacrificed, and lung tissues are collected and are homogenized in 5 ml PBS. 100 µl of the homogenate is inoculated onto Tryficase Soy Agar and the colonies are counted after 1-2 days incubation at 37° C. The results, shown in Table 6, demonstrate the ability of Nu-3 to inhibit pulmonary bacterial infections compared to a PBS control.

TABLE 6

Antibacterial efficacy of liposomal Nu-3 via pulmonary delivery to rats

| Rats | Colony forming units (CFU) × $10^4$ | |
|---|---|---|
|  | PBS control | Nu-3 treatment |
| 1 | 0.78 | 0.48 |
| 2 | 1.60 | 0.54 |
| 3 | 20.00 | 0.86 |
| 4 | 3.10 | 0.16 |
| 5 | 0.12 | 0.30 |
| X ± SE | 5.12±3.8 | 0.46 ± 0.11 |

Example 11

Determination of Antifungal Activity of Nu-3

The efficacy of Nu-3 is tested against two strains of fungal species: *Candida albicans* and *Saccharomyces pastorianus*, in a 24-well plate with a series of dilutions of Nu-3. The first concentration utilized is 30 µl of aqueous Nu-3 with an OD of 25 added to each well, administering diluted doses to subsequent wells, as indicated. In each well, 20 µl of fungal solution (approximately 10 fungal cells) and 150 µl of 10% Sabouraud Dextrose medium are added, and are cultured on a rotating culture plate at 25° C. The fungal growth inhibition is recorded after 24 hrs. As shown in Table 7, Nu-3 markedly suppresses fungal replication and at some concentrations, fungal cells are completely eradicated, as compared to vehicle control.

TABLE 7

In-vitro antifungal efficacy of Nu-3 against *C. albincans* and *S. pastorianus*.

| Fungal | Growth inhibition at different concentration of Nu-3 | | | | | |
|---|---|---|---|---|---|---|
| | 25 OD | 12.5 OD | 6.25 OD | 3.13 OD | 1.56 OD | Control |
| C albicans | − | + | ++ | +++ | +++ | +++ |
| S pastorianus | − | − | − | − | + | +++ |

Example 12

Antibacterial Efficacy of Nu-3 in Humans

The efficacy of Nu-3 to inhibit microbial infection is evaluated in humans. Nu-3 is administered as an aqueous solution at a concentration of 1 g/100 ml (2×) topically 2-4 times per day, approximately 100 µl per dose. The evaluation is performed at tree days post treatment for acute infection and seven days post treatment for chronic infection, as shown in Table 8.

TABLE 8

Antibacterial efficacy of Nu-3 in humans.

| Code | Patients | Sex | Age | Diseases | Severity before treatment* | Severity after treatment* |
|---|---|---|---|---|---|---|
| 1 | L.C. | M | 41 | Oral ulcer | 10+ | 1-2 |
| 2 | C.S. | F | 42 | Nose furuncle | 9 | 1 |
| 3 | J.B. | F | 52 | Local nose infection | 5 | 1 |
| 4 | J.R. | F | 13 | Acne | 4 | 1 |
| 5 | D.B. | F | 51 | Urethritis | 8 | 1 |
| 6 | A.R. | F | 54 | Urethritis | 9 | 4 |
| 7 | L.B. | F | 65 | Urethritis | 7 | 1 |
| 11 | K.C. | M | 67 | Diabetes ulcer | 10+++ | 4 |
| 12 | D.C. | M | 59 | Infection | 10+++ | 5 |
| 13 | F.C. | M | 80 | Diabetes ulcer | 10+++ | 2 |
| 14 | S.H. | F | 60 | Skin infection | 7 | 1 |
| 15 | N.M. | F | 46 | Skin infection | 10+ | 1 |
| 16 | K.M. | F | 8 | Insect bite infection | 5 | 1 |
| 17 | T.B. | M | 55 | Infection from puncture injury | 6 | 1 |
| 21 | J.M. | F | 28 | Streptococcus | 5 | 1 |
| 22 | M.F. | M | 37 | Surgical infection | 8 | 1 |
| 23 | C.G. | F | 64 | Surgical infection | 9 | 1 |
| 24 | K.F. | F | 31 | Fistula | 8 | 1 |
| 25 | R.C. | F | 59 | Fistula | 10 | 2 |
| 26 | P.C. | F | 46 | Fistula | 9 | 4 |
| 30 | B.D. | F | 17 | Acne | 10 | 5 |
| 31 | Z.M. | M | 14 | Acne | 5 | 2 |
| 32 | M.R. | F | 36 | Acne | 6 | 1 |
| 33 | K.Y. | F | 38 | Acne | 6 | 3 |
| 34 | S.G. | M | 17 | Acne | 7 | 1 |
| 35 | M.B. | F | 15 | Acne | 5 | 1 |
| 36 | C.B. | F | 16 | Acne | 5 | 2 |
| 37 | J.F. | F | 28 | Acne | 5 | 2 |
| 38 | M.H. | F | 40 | Acne | 5 | 1 |
| 39 | S.H. | F | 17 | Acne | 5 | 1 |
| 45 | D.W. | F | 42 | Urethritis | 8 | 1 |
| 46 | D.T. | F | 38 | Infection from puncture injury | 7 | 2 |
| 47 | M.J. | F | 40 | Infection from puncture injury | 10+ | 3-4 |
| 48 | T.L. | F | 12 | Acne | 4 | 2 |
| 49 | M.L. | F | 15 | Acne | 5 | 1 |
| 50 | J.B. | F | 57 | Urethritis | 7 | 1 |
| 51 | E.Y. | M | 38 | Folliculitis | 9 | 2 |
| 52 | J.V. | M | 6 | Infection | 10+ | 2 |
| 53 | D.L. | F | 32 | Acne | 4 | 1 |
| 54 | K.S. | F | 17 | Acne | 10 | 1-2 |
| 55 | B.M. | M | 12 | Acne | 6 | 2 |
| 56 | J.C. | M | 16 | Acne | 7 | 1 |
| 57 | J.W. | F | 26 | Acne | 5 | 1 |
| 58 | T.A. | F | 13 | Acne | 5 | 1 |
| 59 | J.H. | M | 15 | Acne | 8 | 2 |
| 60 | B.R. | M | 15 | Acne | 9 | 3 |
| 61 | H.D. | F | 17 | Acne | 10 | 3 |
| 62 | K.M. | F | 8 | Ear infection | 7 | 1 |
| 63 | P.W. | F | 43 | Ear infection | 7 | 1 |
| 64 | M.B. | F | 40 | Ear infection | 7 | 1 |
| 65 | S.M. | F | 33 | Ear infection | 5 | 1 |

*Degree of severity of the infection: 10: most severe; 1: very mild.

Example 13

Antifungal Efficacy of Nu-3 in Humans

Eight patients receive Nu-3 solution three times per day (100 μl of 20 A260 units/ml for each application) for two weeks. At the end of this treatment period the antifungal effect is assessed by clinicians. The results of their evaluation, as shown in Table 9, demonstrate that Nu-3 has strong antifungal effects in humans.

TABLE 9

Antifungal efficacy in-vivo in humans.

| Code | Patients | Sex | Age | Severity before treatment* | Severity after treatment* |
|---|---|---|---|---|---|
| 8 | P.C. | F | 46 | 9 | 1 |
| 9 | K.G. | F | 32 | 5 | 1 |
| 10 | W.P. | F | 51 | 6 | 2 |
| 18 | P.Y. | F | 61 | 7 | 1 |
| 19 | D.A. | M | 77 | 8 | 1 |
| 20 | R.C. | M | 46 | 7 | 1 |
| 28 | T.H. | F | 39 | 7 | 1 |
| 29 | S.L. | F | 42 | 8 | 1 |
| 30 | S.M. | F | 32 | 4 | 1 |

*Degree of severity of the infection: 10: most severe; 1: very mild.

Example 4

In-Vitro Determination of Antiviral Efficacy of Nubiotics

Antiviral activities are determined based on the inhibition of cytopathic effect (CPE) (Snoeck R, Sakuma T, Clercy E D, Rosenberg A. Holy. *Antimicrob Agents Chemother* 1988; 32:1839-1844). HEL cells are seeded in a 96-well plate and 2-4 Cell Culture Infectious Doses ($CCID_{50}$) of the virus (HIV, HSV or HCMV) are added to each well. After absorption for 2 h at 37° C., un-absorbed virus is removed and 100 μl of medium (MEM+2% calf serum) containing Nu-2, Nu-3, or Nu-5 (highest concentration of 100 $A_{260}$ units/ml, with subsequent dilutions) is added. The plate is incubated at 37° C. for 4-6 days, is fixed with 70% ethanol and is stained with 2.5% Giemse solution for 2 h. The plate is washed a further three times with $H_2O$ and air-dried. CPE is monitored and recorded under a microscope and the antiviral activity is expressed as EC50 (μg/ml). All are in triplicates.

Example 14

In-Vivo Antiviral Efficacy of Nu-3 in Humans

Five patients with HSV infection are treated with liposomal Nu-3 at three sprays per day (100 μl of 20 A260 units/ml solution) for two weeks. The patients are evaluated two weeks at that time and the results are shown in Table 10.

TABLE 10

Anti-viral Efficacy of Nu-3 in humans.

| Patient Code | Patients | Sex | Age | Diseases | Diseases status pre-treatment* | Disease status post-treatment* |
|---|---|---|---|---|---|---|
| 40 | C.R. | M | 36 | HSV | 5 | 1 |
| 41 | H.S. | F | 40 | HSV | 4 | 1 |
| 42 | E.B. | F | 11 | HSV | 3 | 1 |
| 43 | M.K. | M | 30 | HSV | 6-7 | 1 |
| 44 | C.W. | F | 57 | HSV | 10 | 1-2 |

*Degree of severity of the infection: 10: most severe; 1: very mild.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound of Formula 2

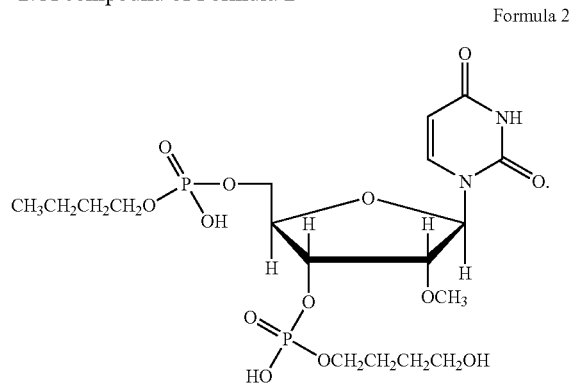

2. A compound of Formula 3

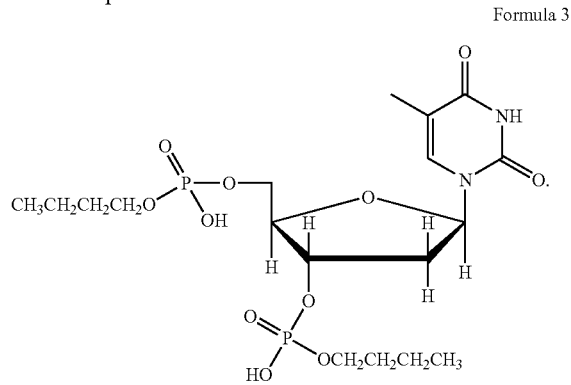

3. A compound of Formula 4

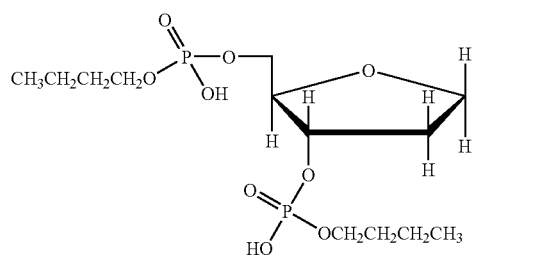

* * * * *

UNITED STATES PATENT AND TRADEMARK OFFICE
CERTIFICATE OF CORRECTION

| | | |
|---|---|---|
| PATENT NO. | : 7,868,162 B2 | Page 1 of 1 |
| APPLICATION NO. | : 11/552951 | |
| DATED | : January 11, 2011 | |
| INVENTOR(S) | : Dale | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 886 days.

Signed and Sealed this
Seventh Day of June, 2011

David J. Kappos
*Director of the United States Patent and Trademark Office*